(12) United States Patent
Kitamura

(10) Patent No.: US 8,577,110 B2
(45) Date of Patent: Nov. 5, 2013

(54) DEVICE, METHOD AND COMPUTER READABLE RECORDING MEDIUM CONTAINING PROGRAM FOR SEPARATING IMAGE COMPONENTS

(71) Applicant: FUJIFILM Corporation, Tokyo (JP)

(72) Inventor: Yoshiro Kitamura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/721,222

(22) Filed: Dec. 20, 2012

(65) Prior Publication Data

US 2013/0108137 A1    May 2, 2013

Related U.S. Application Data

(63) Continuation of application No. 13/419,036, filed on Mar. 13, 2012, now Pat. No. 8,363,915, and a continuation of application No. 12/190,743, filed on Aug. 13, 2008, now Pat. No. 8,155,412.

(30) Foreign Application Priority Data

Aug. 15, 2007   (JP) ................................ 2007-211762
Jun. 6, 2008    (JP) ................................ 2008-148849

(51) Int. Cl.
   *G06K 9/00*   (2006.01)
(52) U.S. Cl.
   USPC ........................................................ 382/128
(58) Field of Classification Search
   USPC ................................................. 382/128, 132
   See application file for complete search history.

(56) References Cited

U.S. PATENT DOCUMENTS

| | | |
|---|---|---|
| 4,851,984 A | 7/1989 | Doi et al. |
| 5,319,549 A | 6/1994 | Katsuragawa et al. |
| 5,343,390 A | 8/1994 | Doi et al. |
| 5,402,338 A | 3/1995 | Ito |
| 5,668,888 A | 9/1997 | Doi et al. |
| 5,931,780 A | 8/1999 | Giger et al. |
| 6,205,348 B1 | 3/2001 | Giger et al. |

(Continued)

FOREIGN PATENT DOCUMENTS

| | | |
|---|---|---|
| JP | 59-010839 A | 1/1984 |
| JP | 5-236351 A | 9/1993 |
| JP | 2005-012248 A | 1/2005 |
| WO | 03/073064 A2 | 9/2003 |

OTHER PUBLICATIONS

Hyvarinen, et al, "Iindependent component analysis," 2001, John Wiley & Sons, pp. v-xvi and 1-12.

(Continued)

*Primary Examiner* — Rodney Fuller
(74) *Attorney, Agent, or Firm* — Sughrue Mion, PLLC

(57) ABSTRACT

A problem inherent to radiographic images, which may occur when an independent component analysis technique is applied to energy subtraction carried out on radiographic images, is solved to achieve separation of image components to be separated with higher accuracy. As preprocessing before the independent component analysis, a spatial frequency band which contains the components to be separated is extracted, pixels of the radiographic images are classified into more than one subsets for each radiographic image based on a value of a predetermined parameter, and/or nonlinear pixel value conversion is applied to the radiographic images based on a value of the predetermined parameter. Alternatively, nonlinear independent component analysis is carried out according to a model using the predetermined parameter.

4 Claims, 15 Drawing Sheets

(56) References Cited

U.S. PATENT DOCUMENTS

| | | |
|---|---|---|
| 6,421,419 B1 | 7/2002 | Sakaida |
| 6,751,341 B2 | 6/2004 | Oosawa |
| 7,315,640 B1 | 1/2008 | Brady et al. |
| 7,680,315 B2 | 3/2010 | Roehrig et al. |
| 8,155,412 B2 * | 4/2012 | Kitamura ............. 382/128 |
| 8,363,915 B2 * | 1/2013 | Kitamura ............. 382/128 |
| 2002/0085671 A1 | 7/2002 | Sakaida |
| 2008/0232667 A1 | 9/2008 | Kitamura et al. |
| 2008/0232668 A1 | 9/2008 | Kitamura et al. |

OTHER PUBLICATIONS

EP Communication, dated Dec. 10, 2009, issued in corresponding EP Application No. 08014391.0, 11 pages.

Jiang et al., "Dual Energy X-ray Image Decomposition by Independent Component Analysis," Proceedings of SPIE Medical Image Acquisistion and Processing, vol. 4549, 2001, pp. 102-107, XP-002558109.

Sarkar et al., "Detection of Rib Shadows in Digital Chest Radiographs," Lecture Notes in Computer Science: Image Analysis and Processing, vol. 1311, 1997, pp. 356-363, XP-002558110.

Rasheed et al., "Rib Suppression in Frontal Chest Radiographs: A Blind Source Separation Approach," Signal Processing and Its Applications 2007, Feb. 2, 2007, pp. 1-4, XP-031280678.

Stahl et al., "Digital Radiography Enhancement by Nonlinear Multiscale Processing," Medical Physics, vol. 27, No. 1, Jan. 1, 2000, pp. 56-65, XP-012010959.

Lehmann et al., "Generalized Image Combinations in Dual KVP Digital Radiography," Medical Physics, vol. 8, No. 5, Sep. 1, 1981, pp. 659-667, XP-000615151.

Ito et al., "Improvement of Detection in Computed Radiography by New Single-Exposure Dual-Energy Subtraction," Proc. SPIE: Medical Imaging VI: Image Processing, vol. 1652, 1992, pp. 386-396, XP-002558168.

Communication pursuant to Article 94(3) EPC, dated Jan. 11, 2011, issued in corresponding EP Application No. 08 014 391.0, 5 pages.

Communication pursuant to Article 94(3) EPC, dated Aug. 2, 2011, issued in corresponding EP Application No. 08014391.0, 5 pages.

Communication, dated Nov. 28, 2011, issued in corresponding EP Application No. 11179288.3, 13 pages.

Chen et al., "Beam Hardening Correction for Computed Tomography Images Using a Postreconstruction Method and Equivalent Tissue Concept," Journal of Digital Imaging, vol. 14, No. 2, Jun. 1, 2001, pp. 54-61, XP001032917.

de Paiva et al., "A beam hardening correction for X-ray microtomography," NDT&E International, vol. 31, No. 1, Feb. 1, 1998, pp. 17-22, XP004292557.

McDavid et al., "Correction for spectral artifacts in cross-sectional reconstruction from x rays," Medical Physics, vol. 4, No. 1, Jan. 1, 1977, pp. 54-57, XP002328195.

Hammersberg et al., "Correction for beam hardening artefacts in computerised tomography," Journal of X-Ray Science and Technology, vol. 8, No. 1, Jan. 1, 1998, pp. 75-93, XP009018945.

Gao et al., "Beam Hardening Correction for Middle-Energy Industrial Computerized Tomography," IEEE Transactions on Nuclear Science, vol. 53, No. 5, Oct. 1, 2006, pp. 2796-2807, XP011149553.

EPO Communication, dated Jul. 31, 2012, issued in corresponding European Application No. 11 179 288.3, 5 pages.

Extended European Search Report, dated Jul. 24, 2012, issued in corresponding European Application No. 12 17 0993.5, 11 pages.

Notice of Grounds for Rejection, dated Sep. 25, 2012, issued in corresponding JP Application No. 2008-148849, 4 pages in English and Japanese.

Communication Pursuant to Article 94(3) EPC, dated Apr. 23, 2013, issued in corresponding EP Application No. 12 170 993.5, 8 pages.

\* cited by examiner

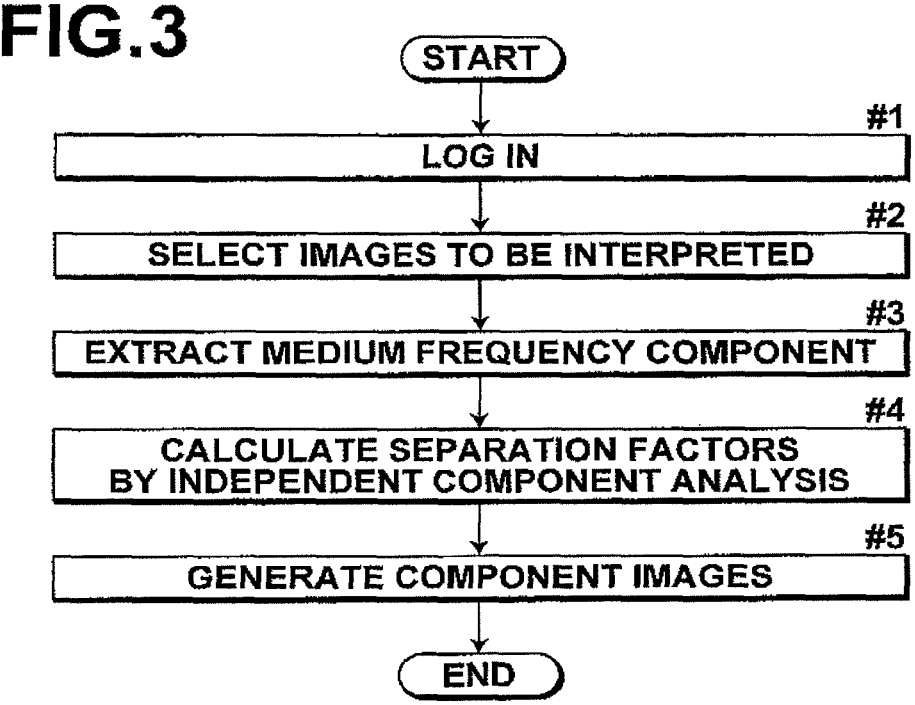
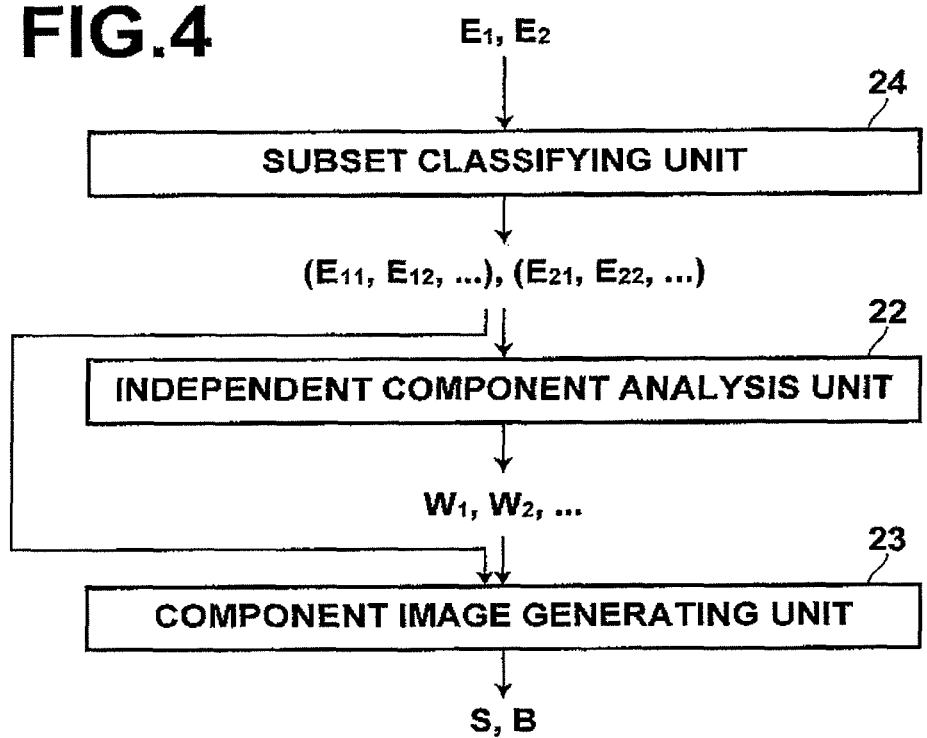

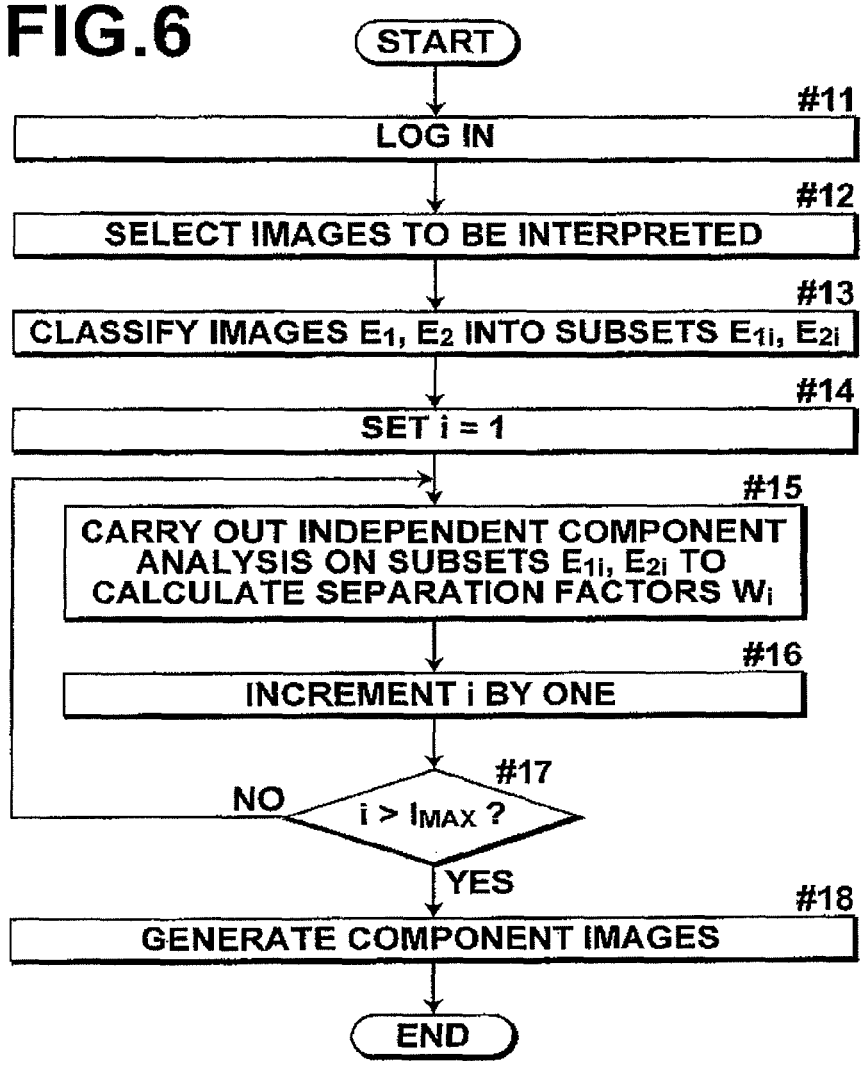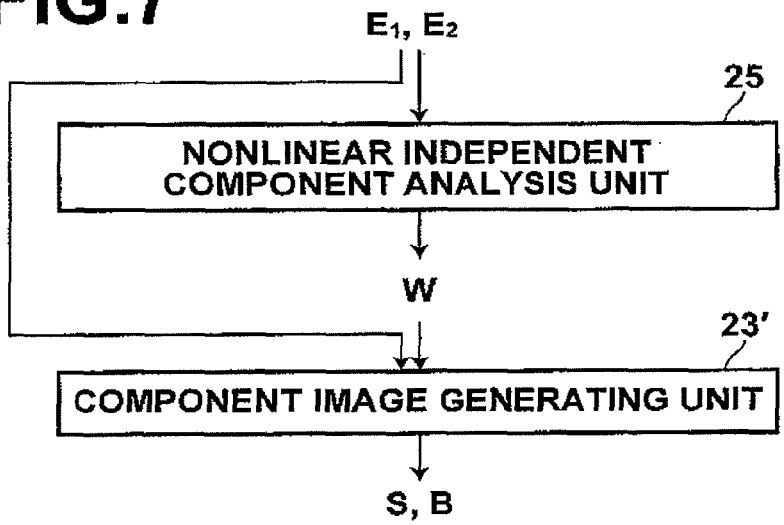

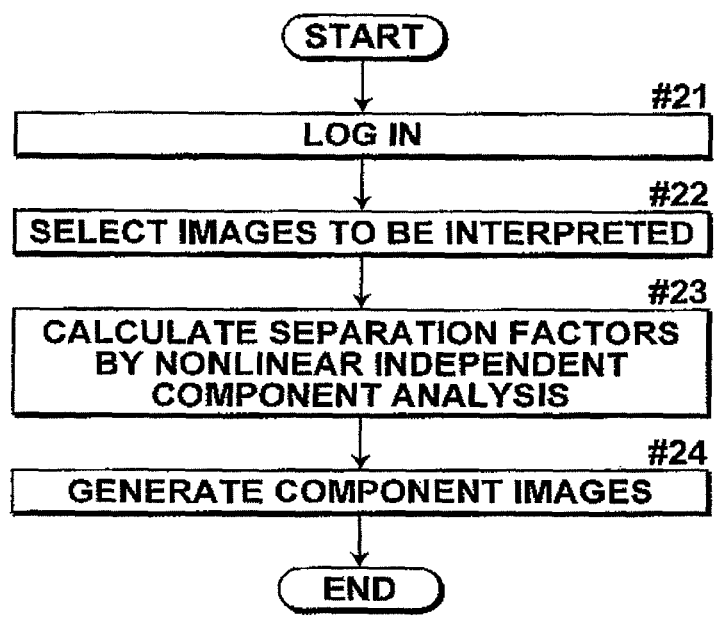

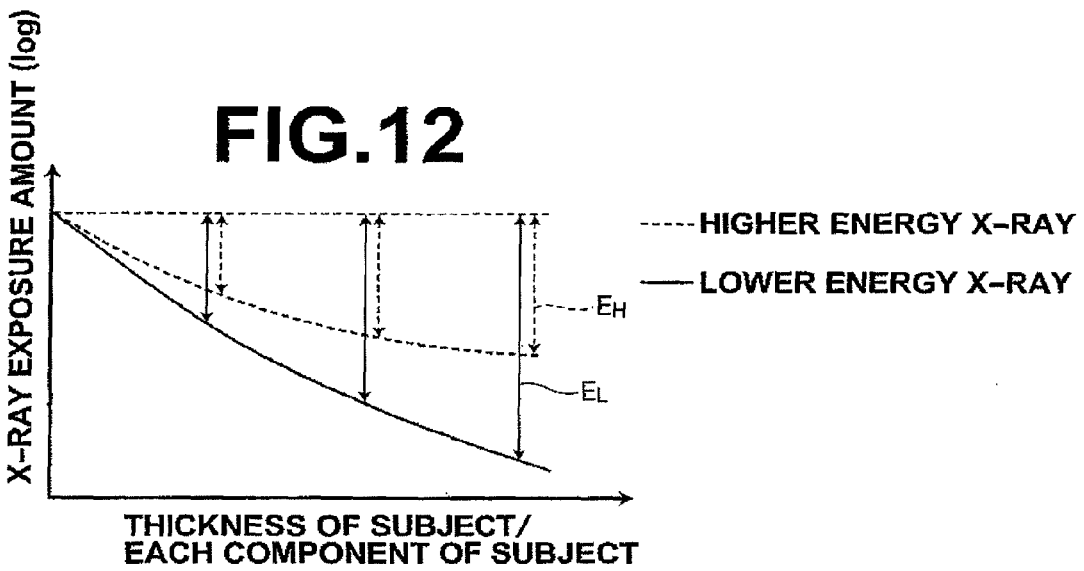
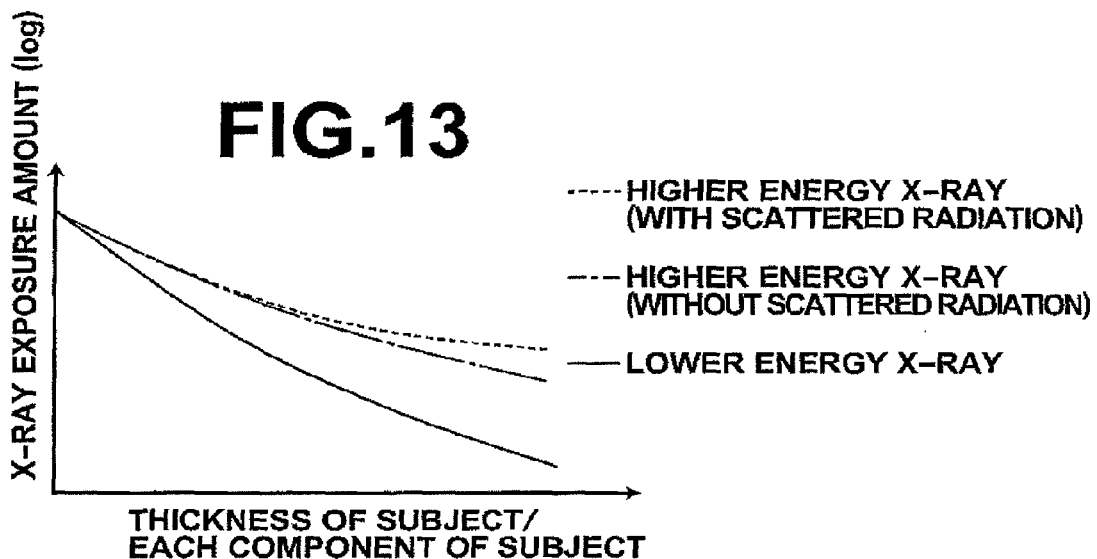

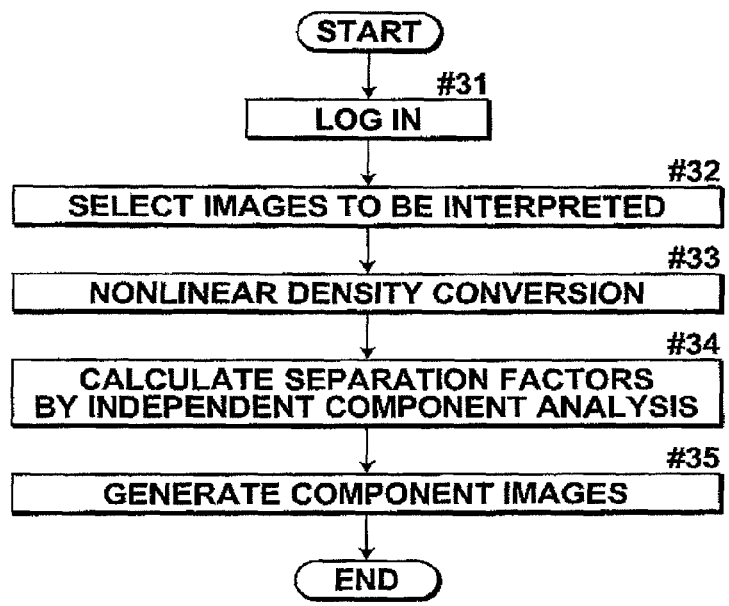
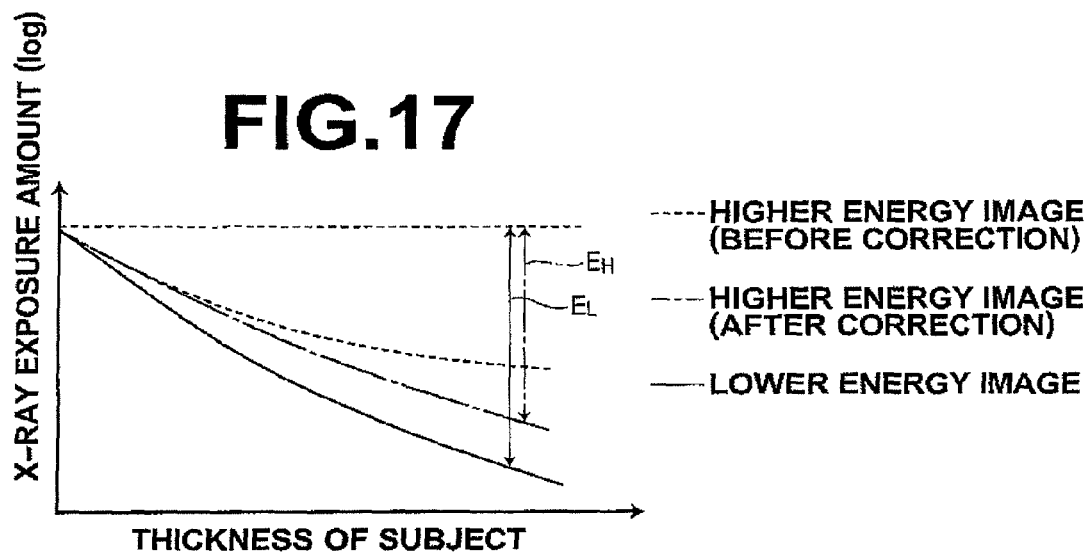

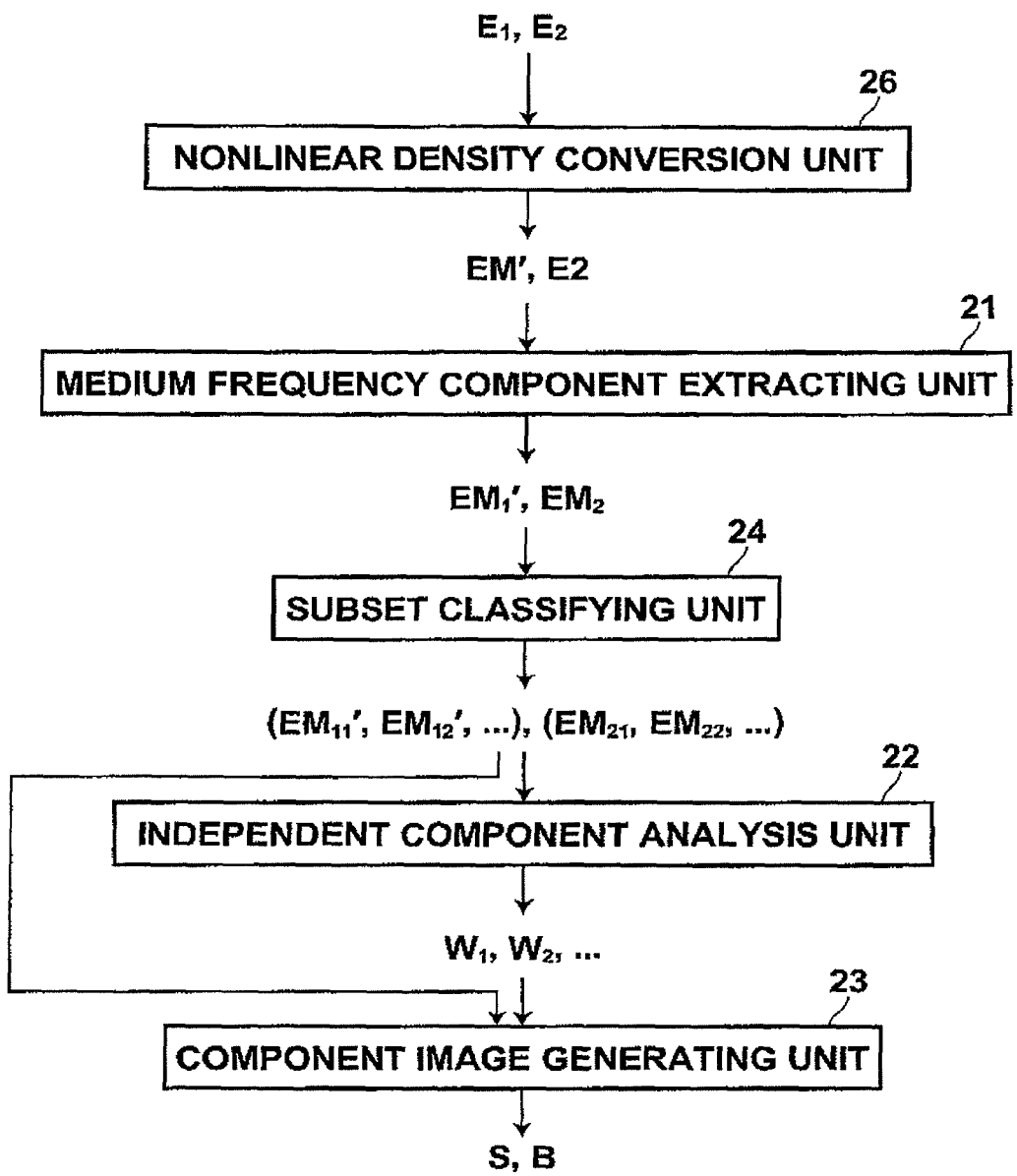

DEVICE, METHOD AND COMPUTER READABLE RECORDING MEDIUM CONTAINING PROGRAM FOR SEPARATING IMAGE COMPONENTS

This application is a continuation of U.S. application Ser. No. 13/419,036, filed Mar. 13, 2012, now U.S. Pat. No. 8,363,915, which is a continuation of U.S. application Ser. No. 12/190,743, filed Aug. 13, 2008, now U.S. Pat. No. 8,155,412, which claims priority to JP 2007-211762, filed Aug. 15, 2007, and JP 2008-148849, filed Jun. 6, 2008, each of which is incorporated herein by reference in its entirety.

BACKGROUND OF THE INVENTION

1. Field of the Invention

The present invention relates to a device and a method for separating particular image components using more than one radiographic images which are taken with radiations having different energy distributions, and a computer readable recording medium containing a program for causing a computer to carry out the method.

2. Description of the Related Art

A technique called energy subtraction has been known in the field of medical image processing. In this technique, two radiographic images of the same subject are taken by applying radiations having different energy distributions to the subject, and image signals representing corresponding pixels of these radiographic images are multiplied with suitable weighting factors and subtraction is carried out between pairs of the corresponding pixels of the images to obtain difference signals, which represent an image of a particular structure. Using this technique, a soft part image formed by removing the bone component from the inputted images or a bone part image formed by removing the soft part component from the inputted images can be generated. Using an image from which parts that are not of interest in diagnosis have been removed for image interpretation, visibility of the part of interest in the image is improved (see, for example, U.S. Pat. No. 6,421,419).

A technique called Independent Component Analysis (ICA) is known. This technique is used to separate a plurality of statistically-independent unknown component signals from a plurality of known observation signals. This technique is applied, for example, to extract voices of respective persons (component signals) from recorded contents (observation signals) which have been obtained by recording the voices of the persons through a plurality of microphones.

It is suggested that this independent component analysis technique is applicable to the above-described energy subtraction. Specifically, an absorption spectrum of a radiation varies depending on the energy level thereof and/or the component of a subject, such as soft parts or bones. That is, a radiographic image obtained by exposure to radiation is a mixture of different component images. Therefore, it is suggested that the independent component analysis technique may be applied to the energy subtraction to separate a plurality of image components (component signals), which represent soft parts and bones, from two radiographic images (observation signals) obtained with radiations having different energy distributions as described above (International Patent Publication No. WO03/073064).

In the independent component analysis technique, it is assumed that the component signals to be separated are statistically independent from each other and that the component signals contained in the observation signals are mixed at constant ratios. In practice, however, it is difficult to satisfy such preconditions, and the individual component signals may not always be restored appropriately.

Therefore, the above-mentioned International Patent Publication No. WO03/073064 proposes a partial independent component analysis approach, in which, when gene expression profiling using cDNA microarrays is carried out according to the independent component analysis, the independent component analysis is applied on a gene informative index subspace containing only differentially expressed genes, rather than using a gene informative index space (the entire observation signal) which contains genes causing separation error, to separate expression levels of the genes (component signals) supplied by malignant and stromal cells. In this approach, component signals obtained through the independent component analysis applied on the entire gene informative index space are repeatedly evaluated according to a predetermined measure to identify a gene informative index subspace, which satisfies the statistical independence condition for the component signals, from the entire observation signal.

The above-mentioned International Patent Publication No. WO03/073064, however, does not teach or suggest a problem and a solution which are inherent to the independent component analysis or the partial independent component analysis being applied to the energy subtraction carried out on radiographic images.

SUMMARY OF THE INVENTION

In view of the above-described circumstances, the present invention is directed to providing a device, a method and a computer readable recording medium containing a program which more appropriately apply the independent component analysis technique to the energy subtraction carried out on radiographic images.

A first aspect of the image component separation device of the invention includes: component separating means for separating more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating means separating the image components by calculating weighted sums using predetermined weighting factors for each corresponding pixel among the radiographic images; and further includes band extracting means for extracting, from each of the radiographic images, an image component of a spatial frequency band containing the predetermined components, wherein the component separating means carries out independent component analysis on the image components of the spatial frequency band extracted by the band extracting means to obtain separation factors for separating the more than one image components from the image components of the spatial frequency band and uses the separation factors as the predetermined weighting factors.

A first aspect of the image component separation method of the invention includes: a component separating step to separate, using a computer, more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating step including separating the image components by calculating weighted sums using predetermined weighting factors for each corresponding pixel among the radiographic images; and prior to the above step, a band extracting step to extract, from each of the radiographic images, using the computer, an image component of a spatial frequency band containing the predetermined components, wherein the component separating step includes carrying out independent component analysis on the image components of the spatial frequency band extracted in the band extracting step to obtain separation factors for separating the more than one image components from the image components of the spatial frequency band and using the separation factors as the predetermined weighting factors.

A first aspect of the computer-readable recording medium containing the image component separation program of the invention contains a program for causing a computer to carry out the first aspect of the image component separation method.

A second aspect of the image component separation device of the invention includes: component separating means for separating more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating means separating the image components by calculating weighted sums using predetermined weighting factors for each corresponding pixel among the radiographic images; and further includes subset classifying means for classifying pixels of the radiographic images into one or more subsets for each of the radiographic images based on a value of a parameter, the parameter being obtained from at least one of the radiographic images and having a predetermined relationship with a thickness of each of the more than one predetermined components or a thickness of the subject at each pixel of the radiographic images, wherein the component separating means carries out independent component analysis on at least one group of corresponding subsets between the radiographic images to obtain separation factors for separating the more than one image components from the subsets, and uses the separation factors as the predetermined weighting factors.

A second aspect of the image component separation method of the invention includes: a component separating step to separate, using a computer, more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating step including separating the image components by calculating weighted sums using predetermined weighting factors for each corresponding pixel among the radiographic images; and prior to the above step, a subset classifying step to classify, using the computer, pixels of the radiographic images into one or more subsets for each of the radiographic images based on a value of a parameter, the parameter being obtained from at least one of the radiographic images and having a predetermined relationship with a thickness of each of the more than one predetermined components or a thickness of the subject at each pixel of the radiographic images, wherein the component separating step includes carrying out independent component analysis on at least one group of corresponding subsets between the radiographic images to obtain separation factors for separating the more than one image components from the subsets, and using the separation factors as the predetermined weighting factors.

A second aspect of the computer-readable recording medium containing the image component separation program of the invention contains a program for causing a computer to carry out the second aspect of the image component separation method.

A modification of the second aspect of the image component separation device of the invention may include: subset classifying means for classifying pixels of more than one radiographic images into one or more subsets for each of the radiographic images based on a value of a parameter, the parameter being obtained from at least one of the radiographic images and having a predetermined relationship with a thickness of each of more than one predetermined components of a subject or a thickness of the subject at each pixel of the radiographic images, each radiographic image being formed by radiation transmitted through the subject, each radiographic image representing degrees of transmission and attenuation through the subject of each of different patterns of radiation having different energy distributions; and component separating means for separating more than one image components respectively representing the more than one predetermined components of the subject from the radiographic images by carrying out independent component analysis on each group of corresponding subsets between the radiographic images to obtain, for each group of the subsets, separation factors for separating each of the image components representing the more than one predetermined components from the subsets, and by calculating, for each group of the subsets, weighted sums for each corresponding pixel among the subsets with using the separation factors as weighting factors.

Similarly, a modification of the second aspect of the image component separation method of the invention may include: a subset classifying step to classify, using a computer, pixels of more than one radiographic images into one or more subsets for each of the radiographic images based on a value of a parameter, the parameter being obtained from at least one of the radiographic images and having a predetermined relationship with a thickness of each of more than one predetermined components of a subject or a thickness of the subject at each pixel of the radiographic images, each radiographic image being formed by radiation transmitted through the subject, each radiographic image representing degrees of transmission and attenuation through the subject of each of different patterns of radiation having different energy distributions; and a component separating step to separate, using the computer, more than one image components respectively representing the more than one predetermined components of the subject from the radiographic images by carrying out independent component analysis on each group of corresponding subsets between the radiographic images to obtain, for each group of the subsets, separation factors for separating each of the image components representing the more than one predetermined components from the subsets, and by calculating, for each group of the subsets, weighted sums for each corresponding pixel among the subsets with using the separation factors as weighting factors.

Further, a modification of the second aspect of the computer-readable recording medium containing the image component separation program of the invention contains a program for causing a computer to carry out the modification of the second aspect of the image component separation method.

A third aspect of the image component separation device of the invention includes: component separating means for separating more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating means separating the image components by calculating weighted sums using predetermined weighting factors for each corresponding pixel among the radiographic images, wherein the component separating means carries out independent component analysis on the radiographic images to obtain separation factors for separating the more than one image components from the radiographic images and uses the separation factors as the predetermined weighting factors, and the independent component analysis is carried out with using a model representing, as a predetermined function, mixing factors representing mixing ratios of the more than one image components in each of the radiographic images using a parameter obtained from at least one of the radiographic images, the parameter having a predetermined relationship with a thickness of each of the more than one predetermined components or a thickness of the subject at each pixel of the radiographic images.

A third aspect of the image component separation method of the invention includes: a component separating step to separate more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating step including separating the image components by calculating weighted sums using predetermined weighting factors for each corresponding pixel among the radiographic images, wherein the component separating step includes carrying out independent component analysis on the radiographic images to obtain separation factors for separating the more than one image components from the radiographic images and using the separation factors as the predetermined weighting factors, and the independent component analysis is carried out with using a model representing, as a predetermined function, mixing factors representing mixing ratios of the more than one image components in each of the radiographic images using a parameter obtained from at least one of the radiographic images, the parameter having a predetermined relationship with a thickness of each of the more than one predetermined components or a thickness of the subject at each pixel of the radiographic images.

A third aspect of the computer-readable recording medium containing the image component separation program of the invention contains a program for causing a computer to carry out the third aspect of the image component separation method.

A fourth aspect of the image component separation device of the invention includes: component separating means for separating more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating means separating the image components by calculating weighted sums using predetermined weighting factors for each corresponding pixel among the radiographic images; and further includes pixel value converting means for applying nonlinear conversion to a pixel value of each pixel of at least one of the radiographic images based on a value of a parameter obtained from at least one of the radiographic images, the parameter having a predetermined relationship with a thickness of each of the more than one predetermined components or a thickness of the subject at each pixel of the radiographic images, the nonlinear conversion bringing the radiographic images closer to achieving a relationship where a ratio between radiation attenuations in the radiographic images is constant regardless of the thickness of each predetermined component or the thickness of the subject, wherein the component separating means carries out independent component analysis on the image converted by the pixel value converting means to obtain separation factors for separating the more than one image components from the converted images and uses the separation factors as the predetermined weighting factors.

A fourth aspect of the image component separation method of the invention includes: a component separating step to separate more than one image components from more than one radiographic images inputted thereto, the image components respectively representing more than one predetermined components in a subject, each radiographic image being formed by radiation transmitted through the subject, each radiographic image representing degrees of transmission and attenuation through the subject of each of different patterns of radiation having different energy distributions, the component separating step including separating the image components by calculating weighted sums using predetermined weighting factors for each corresponding pixel among the radiographic images; and prior to the above step, a pixel value converting step to apply nonlinear conversion to a pixel value of each pixel of at least one of the radiographic images based on a value of a parameter obtained from at least one of the radiographic images, the parameter having a predetermined relationship with a thickness of each of the more than one predetermined components or a thickness of the subject at each pixel of the radiographic images, the nonlinear conversion bringing the radiographic images closer to achieving a relationship where a ratio between radiation attenuations in the radiographic images is constant regardless of the thickness of each predetermined component or the thickness of the subject, wherein the component separating step includes carrying out independent component analysis on the image converted in the pixel value converting step to obtain separation factors for separating the more than one image components from the converted images and uses the separation factors as the predetermined weighting factors.

A fourth aspect of the computer-readable recording medium containing the image component separation program of the invention contains a program for causing a computer to carry out the fourth aspect of the image component separation method.

Details of the present invention will be explained below.

A specific example of the "subject" may be a human body. For example, if the radiographic images represent the chest of the human body, specific examples of the "more than one predetermined components (to be separated)" may be the bone component and the soft part component. The "soft part component" refers to components of connective tissues other than bone tissues (bone component) of a living body, and includes fibrous tissues, adipose tissues, blood vessels, striated muscles, smooth muscles, peripheral nerve tissues (nerve ganglions and nerve fibers), and the like.

The "more than one radiographic images . . . each radiographic image being formed by radiation transmitted through the subject, each radiographic image representing degrees of transmission and attenuation through the subject of each of different patterns of radiation having different energy distributions" to be inputted may be obtained by a multi-shot method in which imaging is carried out more than once using different patterns of radiations having different energy distributions, or may be obtained by a one-shot method in which radiation is applied once to more than one storage phosphor sheets stacked one on the other via an additional filter such as an energy separation filter (they may be in contact to or separated from each other) so that the energy distribution of the radiation transmitted through the subject in the single exposure is varied, and different patterns of the radiation having different energy distributions are detected on these sheets. Analog images recorded on the storage phosphor sheets, which represent degrees of transmission of the radiation through the subject, are converted into digital images by scanning the sheets with excitation light, such as laser light, to generate photostimulated luminescence, and photoelectrically reading the obtained photostimulated luminescence. Besides the above-described storage phosphor sheet, other means, such as a flat panel detector (FPD) employing CMOS, or the like, may be selected as appropriate depending on the imaging method and used for detecting the radiation.

The "group of corresponding pixels between the radiographic images" refers to pixels positionally corresponding to each other with reference to a predetermined structure (such as a site to be observed or a marker) in the radiographic images. If the radiographic images have been taken in a manner that the position of the predetermined structure in the images does not shift between the images, the corresponding pixels are pixels at the same coordinates in the coordinate system in the respective images. However, if the radiographic images have been taken in a manner that the position of the predetermined structure in the images shifts between the images, the images may be aligned with each other through linear alignment using scaling, translation, rotation, or the like, nonlinear alignment using warping or the like, or a combination of any of these techniques. It should be noted that the alignment between the images may be carried out using a method described in U.S. Pat. No. 6,751,341, or any other method known at the time of putting the invention into practice.

The operation to "separate more than one image components . . . respectively representing more than one predetermined components in a subject . . . by calculating weighted sums using predetermined weighting factors for each corresponding pixel among the radiographic images" refers to a so-called energy subtraction technique.

For example, assuming that a total amount of the radiation applied to the subject is $E_0$, attenuation coefficients determined for the respective components (two components in this example) in the subject depending on the energy distribution of the radiation are $\alpha$ and $\beta$, and thicknesses of the respective components are $t_a$ and $t_b$, then, a logarithmic radiation exposure amount E at each pixel of each radiographic image can be expressed as equation (1) below:

$$E = E_0 - (\alpha \cdot t_a + \beta \cdot t_b) \tag{1}$$

Terms $\alpha \cdot t_a$ and $\beta \cdot t_b$ at the right side of equation (1) represent radiation attenuations in the respective components, and imply that the radiographic image reflects mixed influences of the radiation attenuations in the individual components. Each of the terms $\alpha \cdot t_a$ and $\beta \cdot t_b$ is a product of the attenuation coefficient and the thickness of the component, and this implies that the radiation attenuation at each component is dependent on the thickness of the component. In equation (1), assuming that $E' = E_0 - E$, equation (1) can be simplified as equation (2) below:

$$E' = \alpha \cdot t_a + \beta \cdot t_b \tag{2}$$

Since the two radiographic images to be inputted in the invention have different radiation energy distributions, values of the attenuation coefficients differ between the images. Therefore, a suffix "1" or "2" is added to identify each radiographic image, and equation (2) for each radiographic image can be expressed as equations (3) and (4) below:

$$E'_1 = \alpha_1 \cdot t_a + \beta_1 \cdot t_b \tag{3}$$

$$E'_2 = \alpha_2 \cdot t_a + \beta_2 \cdot t_b \tag{4}$$

Based on this model, the operation to separate each component in the images by combining weighted images in the invention means to obtain relational expressions that are independent from the thickness of the component other than the component to be separated by multiplying the respective terms in each of the above equations with appropriate weighting factors to calculate a weighted sum, so that values of the coefficient parts of the terms corresponding to the component other than the component to be separated become 0. Therefore, in order to separate a certain component in the image, it is necessary to determine the weighting factors such that the coefficient part of the term corresponding to the component other than the component to be separated on the right side of each equation becomes 0.

The logarithmic exposure amount E of the radiographic image is a value obtained by log-transforming an amount of the radiation that has transmitted through the subject and reached the radiation detecting means during imaging of the subject. The exposure amount can be obtained by directly detecting the radiation reached the radiation detecting means; however, it is very difficult to detect the exposure amount at each pixel of the radiographic image. Since a pixel value of each pixel of the image obtained on the radiation detecting means is larger as the exposure amount is larger, the pixel values and the exposure amounts can be related to each other. Therefore, the exposure amounts in the above equations can be substituted with pixel values.

The "independent component analysis" is a technique to separate more than one statistically-independent unknown component signals from more than one known observation signals. That is, the component signals are found from the inputted known observation signals such that the statistical independence between the component signals is maximized.

For example, assuming that there are observation signals $x_1$ and $x_2$ each containing mixed two statistically-independent component signals $s_1$ and $s_2$, as in equations (5) and (6) below:

$$x_1(t) = a_{11} s_1(t) + a_{12} s_2(t) \tag{5}$$

$$x_2(t) = a_{21} s_1(t) + a_{22} s_2(t) \tag{6}$$

wherein, $a_{11}$, $a_{12}$, $a_{21}$ and $a_{22}$ are mixing factors representing mixing ratios of the component signals $s_1$ and $s_2$ in the respective observation signals $x_1$ and $x_2$.

Rewriting the equations (5) and (6) as:

$$X = \begin{pmatrix} x_1 \\ x_2 \end{pmatrix}, A = \begin{pmatrix} a_{11} & a_{12} \\ a_{21} & a_{22} \end{pmatrix}, S = \begin{pmatrix} s_1 \\ s_2 \end{pmatrix},$$

then, equation (7) below is obtained:

$$X = AS \quad (7).$$

Assuming that an inverse matrix of the matrix A is W, the component signals $s_1$ and $s_2$ can be restored by calculating equation (8) below:

$$S = WX \quad (8).$$

Components in the matrix W are separation factors for separating the component signals $s_1$ and $s_2$ from the observation signals $x_1$ and $x_2$.

In the independent component analysis, independence between the component signals $s_1$ and $s_2$ is evaluated according to various criteria, and the separation factors (matrix W) and the component signals $s_1$ and $s_2$ are calculated such that the independence between the component signals $s_1$ and $s_2$ is maximized.

Comparing equations (3) and (4) with equations (5) and (6), the radiographic images ($E'_1$, $E'_2$) in the invention correspond to the observation signals $x_1$ and $x_2$, the components ($t_a$, $t_b$) to be separated in the subject correspond to the component signals $s_1$ and $s_2$, and the attenuation coefficients $\alpha_1$, $\beta_1$, $\alpha_2$ and $\beta_2$ correspond to the mixing factors $a_{11}$, $a_{12}$, $a_{21}$ and $a_{22}$. Therefore, by carrying out the independent component analysis on the radiographic images ($E'_1$, $E'_2$), which correspond to the observation signals, the more than one image components representing the more than one predetermined components ($t_a$, $t_b$) in the subject, which correspond to the component signals, can be obtained. The separation factors (matrix W) obtained at this time are used as the weighting factors for calculating weighted sums of the inputted radiographic images.

As examples of the criteria for evaluating the independence in the independent component analysis, negative entropy and mutual information are known. As specific examples of the processing method for determining the independent components such that the independence therebetween is maximized, a fixed-point approach and a gradient method are known. In the invention, any of these known methods can be selected to be applied as appropriate.

It should be noted that the number of component signals to be found in the independent component analysis is not more than the number of the observation signals. Therefore, in the invention, it is necessary to prepare the radiographic images of the number which is not less than the number of the components to be separated in the subject.

The independent component analysis includes linear independent component analysis, in which the mixing factors (matrix A) are always constant, and nonlinear independent component analysis, in which the mixing factors are defined by a parameter and are not always constant. The third aspect of the invention corresponds to an aspect in which the nonlinear independent component analysis technique is applied.

As a specific example of the operation to "extract, from each of the radiographic images, an image component of a spatial frequency band containing the predetermined components" in the first aspect of the invention, in a case where the image components representing the bone component and the soft part component are separated from the radiographic images of the human body, which is the subject, an image component of the medium frequency band that includes the spatial frequency band corresponding to the thickness of the bone of the human body may be extracted.

Specific examples of the "parameter being obtained from at least one of the radiographic images and having a predetermined relationship with a thickness of each of the more than one predetermined components or a thickness of the subject at each pixel of the radiographic images" in the second, third and fourth aspects of the invention may include a radiation amount at each pixel of one of the radiographic images, a logarithmic value of the radiation amount, a difference between logarithmic values of radiation amounts at each pair of corresponding pixels between two of the radiographic images, and a logarithmic value of a ratio between radiation amounts at each pair of the corresponding pixels. It should be noted that the logarithmic value of the radiation amount can be replaced with a pixel value at each pixel of each image, as described above.

In the second aspect of the invention, the classification into the subsets may be carried out with excluding a region in the radiographic images having a radiation attenuation lower than a first reference value and/or a region in the radiographic images having a radiation attenuation higher than a second reference value. The first reference value may be around 0 to exclude regions where the radiation has scarcely attenuated. The second reference value may be around the maximum attenuation value to exclude regions where most of the radiation has attenuated.

In the second aspect of the invention, only one subset may be extracted to apply the independent component analysis to the one subset to obtain the separation factors, and the obtained separation factors may be applied to the entire image. Alternatively, the images may be classified into more than one subsets to apply the independent component analysis to each classified subset to obtain the separation factors for each subset, and the separation factors for each subset may be used as the predetermined weighting factors to separate the image components.

The "bringing the radiographic images closer to achieving a relationship where a ratio between radiation attenuations in the radiographic images is constant regardless of the thickness of each predetermined component or the thickness of the subject" in the fourth aspect of the invention means that, for example, in a relationship between the thickness of the subject or each component of the subject and the X-ray exposure amount (log) shown in FIG. 12, achieving a relationship where a ratio between an X-ray attenuation $E_H$ in the higher energy image and an X-ray attenuation $E_L$ in the lower energy image of the radiographic images is constant regardless of the thickness of the subject or each component of the subject.

In the fourth aspect of the invention, if the radiographic images are formed by a multi-shot method, the pixel value conversion may be carried out to relatively increase, within regions having larger radiation attenuation in the radiographic images, a gain in one of the radiographic images formed by exposure to higher energy radiation so that the gain in the one of the radiographic images becomes larger than a gain in the other of the radiographic images formed by exposure to lower energy radiation (see FIG. 15), or to relatively decrease a gain in one of the radiographic images formed by exposure to lower energy radiation so that the gain in the one of the radiographic images becomes smaller than a gain in the other of the radiographic images formed by exposure to higher energy radiation (see FIG. 18).

Further, in the fourth aspect of the invention, if the radiographic images are formed by a one-shot method, the pixel value conversion may be carried out to relatively decrease, within regions having larger radiation attenuation in the radiographic images, a gain in one of the radiographic images formed by exposure to higher energy radiation so that the gain in the one of the radiographic images becomes smaller than a gain in the other of the radiographic images formed by exposure to lower energy radiation (see FIG. 18), or to relatively increase a gain in one of the radiographic images formed by exposure to lower energy radiation so that the gain in the one of the radiographic images becomes larger than a gain in the other of the radiographic images formed by exposure to higher energy radiation (see FIG. 15).

Furthermore, in the fourth aspect of the invention, the "more than one radiographic images" to be inputted to calculate the weighted sums may be radiographic images subjected to the pixel value conversion or radiographic images before the conversion.

BRIEF DESCRIPTION OF THE DRAWINGS

FIG. 3 is a flow chart illustrating the flow of an image component separation process and relating operations according to the first embodiment of the invention, FIG. 4 is a block diagram schematically illustrating the configuration of an image component separating device and peripheral elements according to a second embodiment of the invention, FIG. 6 is a flow chart illustrating the flow of an image component separation process and relating operations according to the second embodiment of the invention, FIG. 7 is a block diagram schematically illustrating the configuration of an image component separating device and peripheral elements according to a third embodiment of the invention, FIG. 11 is a flow chart illustrating the flow of an image component separation process and relating operations according to the third embodiment of the invention, FIG. 12 schematically shows a relationship between a thickness of a subject or each component of the subject and an X-ray exposure amount (log), FIG. 13 schematically shows an influence exerted by scattered radiation on the relationship between the thickness of the subject or each component of the subject and the X-ray exposure amount (log), FIG. 16 is a flow chart illustrating the flow of an image component separation process and relating operations according to the fourth embodiment of the invention, FIG. 17 shows a change in the relationship between the thickness of the subject and the X-ray exposure amount (log) achieved by the nonlinear density conversion carried out on a higher energy image, FIG. 22 is a block diagram schematically illustrating the configuration of an image component separating device and peripheral elements according to yet another modification made on the embodiments of the invention.

DESCRIPTION OF THE PREFERRED EMBODIMENTS

Hereinafter, embodiments of the present invention will be described with reference to the drawings.

Figure 1:
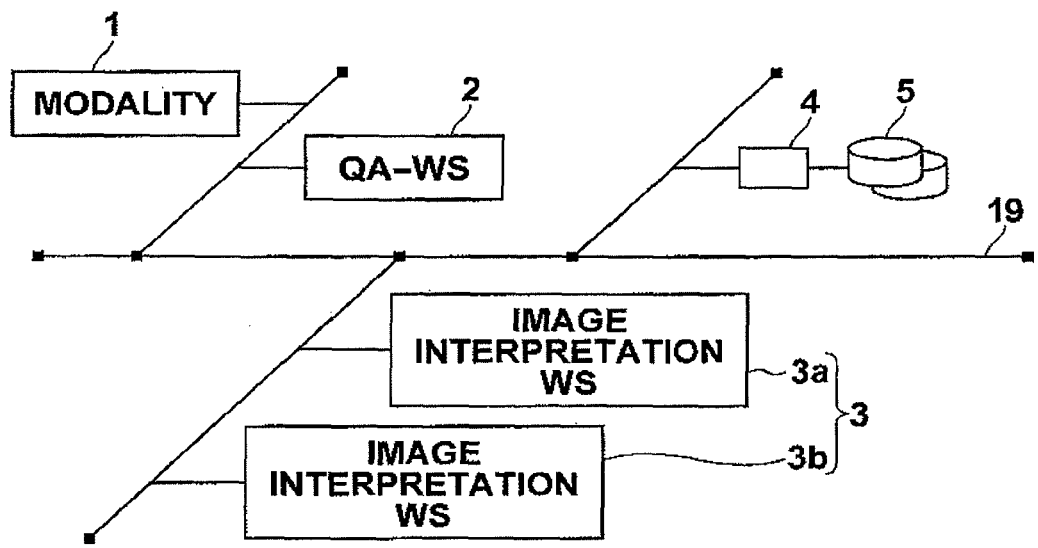
FIG. 1 is a diagram illustrating the schematic configuration of a medical information system incorporating an image component separation device according to embodiments of the invention.

FIG. 1 illustrates the schematic configuration of a medical information system incorporating an image component separation device according to embodiments of the invention. As shown in the drawing, the system includes an imaging apparatus (modality) 1 for taking medical images, an image quality assessment workstation (QA-WS) 2, an image interpretation workstation 3 (3a, 3b), an image information management server 4 and an image information database 5, which are connected via a network 19 so that they can communicate with each other. These devices in the system other than the database are controlled by a program that has been installed from a recording medium such as a CD-ROM. Alternatively, the program may be downloaded from a server connected via a network, such as the Internet, before being installed.

The modality 1 includes a device that takes images of a site to be examined of a subject to generate image data of the images representing the site, and adds the image data with accompanying information defined by DICOM standard to output them as the image information. The accompanying information may be defined by a manufacturer's (such as the manufacturer of the modality) own standard. In this embodiment, the image information of the images taken with an X-ray apparatus and converted into digital image data by a DR apparatus or a CR apparatus is used. The DR apparatus is formed by an X-ray generating unit and an X-ray detector, in which the X-ray generating unit emits an X-ray from an X-ray tube at a tube voltage applied by an X-ray high-voltage generating unit, and the X-ray transmitted through a subject is detected by a flat panel detector (FPD) and converted into electric charges and stored to be converted into digital image data. The CR apparatus is formed by an X-ray imaging unit and an image reading unit. The X-ray imaging unit records radiographic image information of a subject on a storage phosphor sheet IP including a sheet-like storage phosphor layer. The image reading unit scans the storage phosphor sheet IP, which carries the image information recorded by the X-ray imaging unit, with excitation light, such as laser light, to generate photostimulated luminescence, and photoelectrically reads the obtained photostimulated luminescence to obtain an analog image signal. Then, the analog image signal is subjected to logarithmic conversion and is digitalized to generate digital image data. It should be noted that, in the embodiments of the invention, it is preferred to use the DR apparatus when images formed through a multi-shot method are used. Other specific examples of the modality include CT (Computed Tomography), MRI (Magnetic Resonance Imaging), PET (Positron Emission Tomography), and ultrasonic imaging apparatuses. Further, imaging of a selectively accumulated contrast agent with the X-ray apparatus, or the like, may be carried out. It should be noted that, in the following description, a set of the image data representing the subject and the accompanying information thereof is referred to as the "image information". That is, the "image information" includes text information relating to the image.

The QA-WS2 is formed by a general-purpose processing unit (computer), one or two high-definition displays and an input device such as a keyboard and a mouse. The processing unit has software installed therein for assisting operations by the medical technologist. Through functions implemented by execution of the software program, the QA-WS2 receives the image information compliant to DICOM from the modality 1, and applies a standardizing process (EDR process) and processes for adjusting image quality to the received image information. Then, the QA-WS2 displays the image data contained in the processed image information and contents of the accompanying information on a display screen to prompt the medical technologist to check them. Thereafter, the QA-WS2 transfers the image information checked by the medical technologist to the image information management server 4 via the network 19, and requests registration of the image information in the image information database 5.

The image interpretation workstation 3 is used by the imaging diagnostician for interpreting the image and preparing an image interpretation report. The image interpretation workstation 3 is formed by a processing unit, one or two high-definition display monitors and an input device such as a keyboard and a mouse. In the image interpretation workstation 3, operations such as request for viewing an image to the image information management server 4, various image processing on the image received from the image information management server 4, displaying the image, automatic detection and highlighting or enhancement of an area likely to be a lesion in the image, assistance to preparation of the image interpretation report, request for registering the image interpretation report in an image interpretation report server (not shown) and request for viewing the report, and displaying the image interpretation report received from the image interpretation report server are carried out. The image component separation device of the invention is implemented on the image interpretation workstation 3. It should be noted that the image component separation process of the invention, and various other image processing, image quality and visibility improving processes, such as automatic detection and highlighting or enhancement, of a lesion candidate and image analysis may not be carried out on the image interpretation workstation 3, and these operations may be carried out on a separate image processing server (not shown) connected to the network 19, in response to a request from the image interpretation workstation 3.

The image information management server 4 is formed by a general-purpose computer having a relatively high processing capacity on which a software program, which implements a function of a database management system (DBMS), is installed. The image information management server 4 includes a large capacity storage forming the image information database 5. The storage may be a large-capacity hard disk device connected to the image information management server 4 via the data bus, or may be a disk device connected to a NAS (Network Attached Storage) or a SAN (Storage Area Network) connected to the network 19.

The image information database 5 stores the image data representing the subject image and the accompanying information registered therein. The accompanying information may include, for example, an image ID for identifying each image, a patient ID for identifying the subject, an examination ID for identifying the examination, a unique ID (UID) allocated for each image information, examination date and time when the image information was generated, the type of the modality used in the examination for obtaining the image information, patient information such as the name, the age and the sex of the patient, the examined site (imaged site), imaging information (imaging conditions such as a tube voltage, configuration of a storage phosphor sheet and an additional filter, imaging protocol, imaging sequence, imaging technique, whether a contrast agent was used or not, lapsed time after injection of the agent, the type of the dye used, radionuclide and radiation amount), and a serial number or collection number of the image in a case where more than one images were taken in a single examination. The image information may be managed in a form, for example, of XML or SGML data.

When the image information management server 4 has received a request for registering the image information from the QA-WS2, the image information management server 4 converts the image information into a database format and registers the information in the image information database 5.

Further, when the image management server 4 has received a viewing request from the image interpretation workstation 3 via the network 19, the image management server 4 searches through the records of image information registered in the image information database 5 and sends the extracted image information to the image interpretation workstation 3 which has sent the request.

As the user, such as the imaging diagnostician, requests for viewing an image for interpretation, the image interpretation workstation 3 sends the viewing request to the image management server 8 and obtains image information necessary for the image interpretation. Then, the image information is displayed on the monitor screen and an operation such as automatic detection of a lesion is carried out in response to a request from the imaging diagnostician.

The network 19 is a local area network connecting various devices within a hospital. If, however, another image interpretation workstation 3 is provided at another hospital or clinic, the network 19 may include local area networks of these hospitals connected via the Internet or a dedicated line. In either case, the network 9 is desirably a network, such as an optical network, that can achieve high-speed transfer of the image information.

Figure 2:
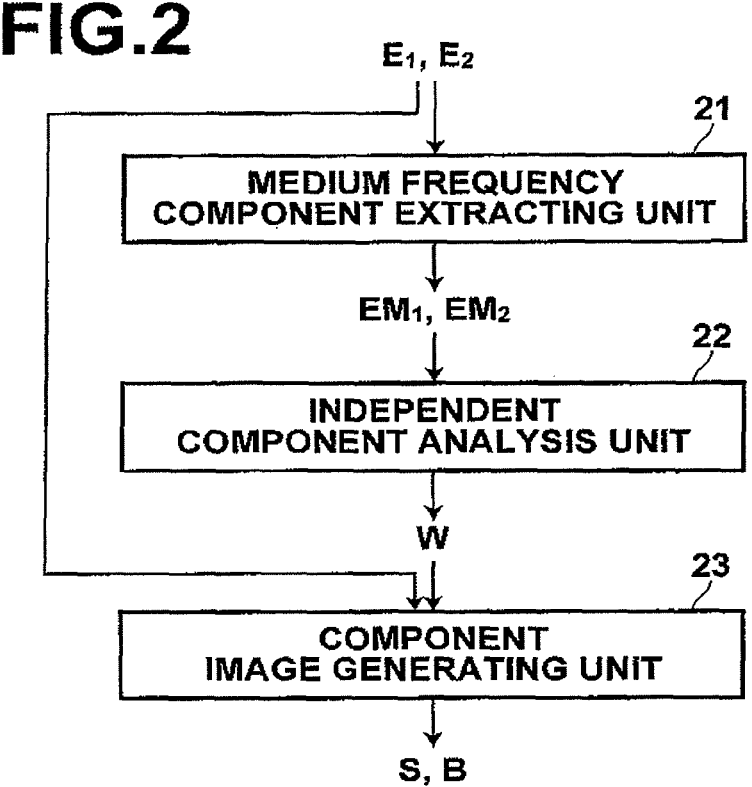
FIG. 2 is a block diagram schematically illustrating the configuration of an image component separating device and peripheral elements according to a first embodiment of the invention.

Now, functions of an image component separation device and peripheral elements according to a first embodiment of the invention are described in detail. FIG. 2 is a block diagram schematically illustrating the configuration and data flow of the image component separation device. As shown in the drawing, this device includes a medium frequency component extracting unit 21, an independent component analysis unit 22 and a component image generating unit 23.

The medium frequency component extracting unit 21 extracts image components ($EM_1$, $EM_2$) of a medium frequency band, which contains a spatial frequency band corresponding to the thickness of the bone of the human body, from the respective inputted radiographic images ($E_1$, $E_2$) using a filter, or the like, which is adjusted to extract a spatial frequency component corresponding to the thickness of the bone of the human body depending on a pixel pitch (scanning resolution) of the images. Specifically, the medium frequency component extracting unit 21 generates a first blur image using a first filter which cuts spatial frequency components having higher spatial frequencies than the spatial frequency components corresponding to the thickness of the bone and generates a second blur image 2 using a second filter which cuts the spatial frequency components corresponding to the thickness of the bone and spatial frequency components having higher spatial frequencies than the spatial frequency components corresponding to the thickness of the bone, and then subtracts the second blur image from the first blur image to obtain image components ($EM_1$, $EM_2$) of the medium frequency band. Alternatively, the image components ($EM_1$, $EM_2$) of the medium frequency band may be obtained by using filters which cut spatial frequency components having higher spatial frequencies than the spatial frequency components corresponding to the thickness of the bone and those having lower spatial frequencies than the spatial frequency components corresponding to the thickness of the bone. Further alternatively, the images ($EM_1$, $EM_2$) of the medium frequency band may be extracted using multiresolution decomposition, in which the inputted image is downsampled to obtain a medium resolution image, this medium resolution image is further downsampled to obtain a low resolution image, this low resolution image is upsampled, and a difference between the upsampled low resolution image and the medium resolution image is calculated to extract the medium frequency band images ($EM_1$, $EM_2$). The downsampling is achieved by using a Gaussian low-pass filter with $\sigma=1$ and ½ pixel skipping of the inputted images, and the upsampling is achieved by using cubic B-spline interpolation.

The independent component analysis unit 22 carries out the independent component analysis on inputted two pieces of image data, which correspond to the observation signals, and calculates separation factors for separating the soft part component and the bone component, which correspond to the independent components, from the images. In this embodiment, explanation is given on an example using a Fast ICA algorithm that estimates the independent components such that a negative entropy is maximized using a fixed-point approach.

Assuming that pixel values of each pair of corresponding pixels between the inputted two pieces of image data are $x_1$ and $x_2$, image components representing the soft part component and the bone component to be separated are $y_1$ and $y_2$, and mixing factors for the respective image components are $a_{11}$, $a_{12}$, $a_{21}$ and $a_{22}$, then, $x_1$ and $x_2$ can be expressed as equations (9) and (10) below:

$$x_1 = a_{11} y_1 + a_{12} y_2 \quad (9),$$

$$x_2 = a_{21} y_1 + a_{22} y_2 \quad (10).$$

Rewriting the equations (9) and (10) as:

$$X = \begin{pmatrix} x_1 \\ x_2 \end{pmatrix}, A = \begin{pmatrix} a_{11} & a_{12} \\ a_{21} & a_{22} \end{pmatrix}, Y = \begin{pmatrix} y_1 \\ y_2 \end{pmatrix},$$

then, equation (11) below is obtained:

$$X = AY \quad (11).$$

Therefore, assuming that an inverse matrix of the matrix A is W, equation (12) below is obtained:

$$Y = WX \quad (12).$$

Under this assumption, first, preprocessing to decorrelate the observation signals is carried out as follows:

Whitened data $\tilde{X}$ of data X is obtained. Specifically, for data $X_0$, which is obtained such that an average of the data X is 0, a covariance matrix thereof is:

$$C_{X0} = E\{X_0 X_0^T\}.$$

Then, a matrix formed by eigenvectors e of $C_{X0}$ is:

$$E = \{e_1 \ldots e_n\}, \text{ and}$$

a diagonal matrix formed by eigenvalues d of $C_{X0}$ is:

$$D = \mathrm{diag}(d_1 \ldots d_n),$$

which are calculated using principal component analysis. Therefore, the whitened data $\tilde{X}$ of the data X is obtained by equation (13) below:

$$\tilde{X} = D^{-1/2} E^T X_0 \quad (13).$$

Here, from $E^T E = E E^T = I$ (I is a unit matrix) and $C_{X0} = E D E^T$, $$E\{\tilde{X}\tilde{X}^T\} = D^{-1/2} E^T E D E^T E D^{-1/2} = I,$$

and therefore $\tilde{X}$ is white.

Then, suitable initial values of two load vectors $w_1$ and $w_2$, which form components of the matrix W representing the separation factors, are determined using, for example, random numbers. At this time, standardization is carried out such as a norm of each vector is 1. It should be noted that $W = (w_1, w_2)^T$.

Further, the next operations (a) and (b) are repeated until convergence is reached. The convergence here refers to that, for each of $w_1$ and $w_2$, directions of the vector before and after update are about the same, i.e., a change in the value of updated $w_i$ is sufficiently small.

(a) For $i=1, 2$, $w_i$ is updated according to expression (14) below:

$$w_i \leftarrow E\{\tilde{X} g(w_i^T \tilde{X})\} - E\{g'(w_i^T \tilde{X})\} w_i \quad (14).$$

Here, assuming that an approximation function of a density function of the restored signals according to the maximum entropy principle is G, g is a differential of G. For example, it is preferred that $g(y) = \tanh(ay)$, or may also be $y \exp(-y^2/2)$ or $y^3$. a is a constant that satisfies $1 \leq a \leq 2$, and 1 is often selected for a.

(b) W is updated such that the elements ($w_1$, $w_2$) of W are perpendicular to each other, according to expression (15) below:

$$W \leftarrow (WW^T)^{-1/2} W \quad (15).$$

Using the matrix W estimated through the above-described procedure, each independent component Y is estimated according to equation (16) below:

$$Y = W\tilde{X} \quad (16).$$

Details of the above operations are disclosed, for example, in "Detailed explanation of independent component analysis—New world of signal analysis" (original title: Independent Component Analysis), written by Hyvärinen et al, translated by Iku Nemoto and Masaki Kawakatsu, Tokyo Denki University Press, February, 2005.

The component image generating unit 23 uses the inputted separation factors as weighting factors to calculate weighted sums for each corresponding pixel between the inputted two images to generate two component images representing the soft part component and the bone component, respectively. That is, the inputted separation factors are applied to all the spatial frequency bands to generate the soft part image and the bone part image.

The corresponding pixels between the images may be identified by detecting a structure, such as a marker or a rib cage, in the images and aligning the images with each other based on the detected structure through a known linear or nonlinear transformation using the detected structure as a reference. Alternatively, the two images may be taken with an X-ray apparatus having an indicator for indicating timings for breathing of the subject (see, for example, Japanese Unexamined Patent Publication No. 2005-012248) so that the two images are taken at the same phase of breathing. In this case, the corresponding pixels can simply be those at the same coordinates in the images, without need of alignment between the images.

Now, workflow and data flow of the image interpretation using an image component separation process according to the first embodiment of the invention are described with reference to the flow chart shown in FIG. 3 and the block diagram shown in FIG. 2.

First, the imaging diagnostician carries out user authentication with a user ID, a password and/or biometric information such as a finger print on the image interpretation workstation 3 for gaining access to the medical information system (#1)

If the user authentication is successful, a list of images to be examined (interpreted) based on an imaging diagnosis order issued by an ordering system is displayed on the display monitor. Then, the imaging diagnostician selects an examination (imaging diagnosis) containing the images to be interpreted $E_1$, $E_2$ from the list of images to be examined through the use of the input device such as a mouse. The image interpretation workstation 3 sends to the image information management server 4 a viewing request with image IDs of the selected images $E_1$ and $E_2$ as the search key. As the image information management server 4 receives this request, the server 4 searches through the image information database 5 and obtains image files (designated by the same symbol E as the images, for convenience) of the images to be interpreted $E_1$, $E_2$, and sends the image files $E_1$ and $E_2$ to the image interpretation workstation 3 that has sent the request. The image interpretation workstation 3 receives the image files $E_1$ and $E_2$ (#2).

Then, the image interpretation workstation 3 analyzes the content of the imaging diagnosis order, and starts a process for generating component images S and B of the soft part component and the bone component separated from the received images $E_1$ and $E_2$, i.e., a program for causing the image interpretation workstation 3 to function as the image component separation device according to the invention.

According to the started program, the medium frequency component extracting unit 21 extracts the image components $EM_1$ and $EM_2$ of the medium frequency band respectively from the inputted radiographic images $E_1$ and $E_2$ (#3), the independent component analysis unit 22 carries out the independent component analysis on the inputted two medium frequency band images $EM_1$ and $EM_2$, which correspond to the observation signals, to calculate separation factors W for separating the soft part component and the bone component, which correspond to the independent components, from the images (#4), and the component image generating unit 23 uses the separation factors W as the weighting factors to calculate weighted sums for each corresponding pixel between the original two radiographic images $E_1$ and $E_2$ to generate the two component images S and B representing the soft part component and the bone component (#5).

The generated component images S and B are displayed on the display monitor of the image interpretation workstation 3, and are used for image interpretation by the imaging diagnostician.

As described above, in the medical information system incorporating the image component separation device according to the first embodiment of the invention, the medium frequency component extracting unit 21 extracts the image components $EM_1$ and $EM_2$ of the medium frequency band, which contains the spatial frequency band corresponding to the thickness of the bone of the human body, from the inputted radiographic images $E_1$ and $E_2$. Thus, the low frequency band (a spatial frequency band corresponding to structures which are thicker than the thickness of the bone of the human body), where the bone part component are hardly present, and the high frequency band, where the noise is dominant, of the original images $E_1$ and $E_2$ are excluded from the data to be inputted to the independent component analysis unit 22, and the independent component analysis is carried out only on the image components $EM_1$ and $EM_2$ of the medium frequency band, where much of the bone component and the soft part component are present. This minimizes the influence of the noise and improves the robustness of the operation to obtain the separation factors W, thereby allowing separation of the soft part component S and the bone part component B with higher accuracy.

FIG. 4 is a block diagram schematically illustrating the configuration of and data flow in an image component separation device according to a second embodiment of the invention. As shown in the drawing, this device includes a subset classifying unit 24, the independent component analysis unit 22 and the component image generating unit 23.

The subset classifying unit 24 classifies the pixels of the inputted radiographic images into more than one subsets for each image based on a value of a difference between logarithmic radiation amount values of each pair of corresponding pixels of the inputted two radiographic images.

As mentioned above, in actual radiographic images, attenuation coefficients of the soft parts and the bone parts are smaller at portions where the thickness of the subject is greater, due to influence of the beam hardening. Therefore, in a single observation signal in linear independent component analysis, the component signals are mixed with different mixing factors, and subsets of the component signals which are mixed with different mixing factors act as noise to each other during estimation of the independent components.

Figure 5A:
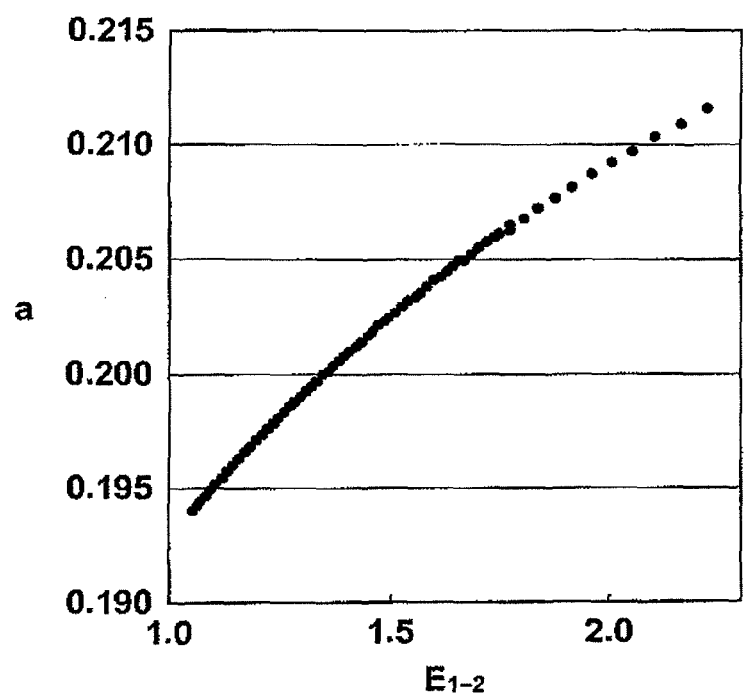
FIGS. 5A and 5B show examples of a relationship between an attenuation coefficient and a logarithmic radiation amount difference.
Figure 5B:
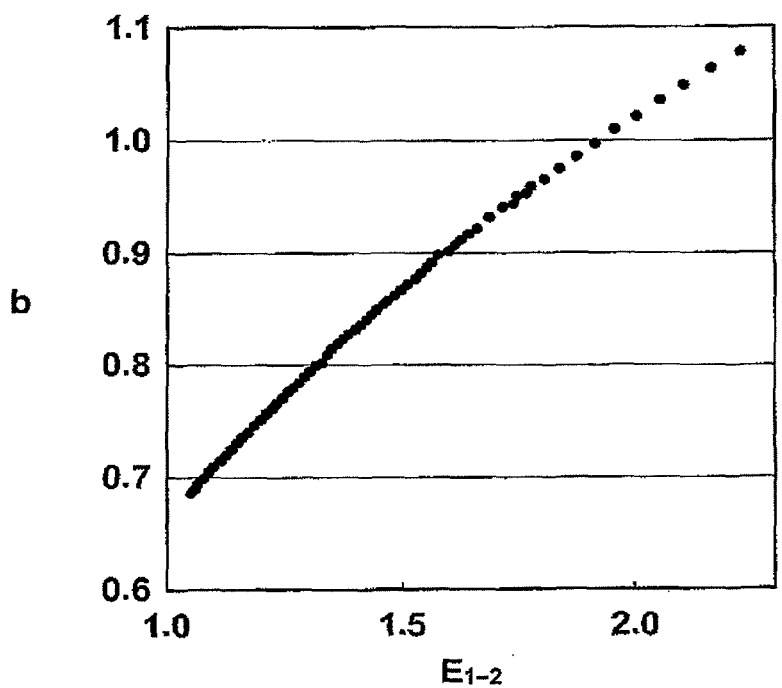

It is known that the attenuation coefficient is dependent on a difference between logarithmic amounts of the inputted two radiographic images, i.e., a difference between pixel values of each pair of corresponding pixels (see U.S. Pat. No. 6,421,419). FIG. 5A shows a relationship between an attenuation coefficient a of the soft part and a logarithmic radiation amount difference $E_{1-2}$, and FIG. 5B shows a relationship between an attenuation coefficient b of the bone part and the logarithmic radiation amount difference $E_{1-2}$. These relationships have been obtained through experiments.

The subset classifying unit 24 calculates a difference between pixel values of each pair of corresponding pixels of the inputted two radiographic images, and carries out histogram analysis on the calculated differences to divide each of the inputted radiographic images into more than one subsets. Thus, a correspondence relationship based on a correspondence relationship between the corresponding pixels is also maintained between the subsets of the two radiographic images.

It should be noted that criteria for the division into the subsets may be a ratio between values of each pair of pixels, or pixel values of one of the inputted radiographic images may be used without any conversion, instead of the difference between values of each pair of pixels.

Operations carried out by the independent component analysis unit 22 and the component image generating unit 23 are the same as those described in the first embodiment.

Now, workflow and data flow of the image interpretation using an image component separation process according to the second embodiment of the invention are described with reference to the flow chart shown in FIG. 6 and the block diagram shown in FIG. 4.

First, similarly to the first embodiment, user authentication of the imaging diagnostician is carried out (#11), and the imaging diagnostician selects and obtains images $E_1$ and $E_2$ to be interpreted (#12). Then, the image interpretation workstation 3 starts a program of the image component separation device according to the second embodiment of the invention, based on contents of an image diagnosis order.

According to the started program, the subset classifying unit 24 classifies the inputted radiographic images $E_1$ and $E_2$ into more than one subsets $E_{1i}$, $E_{2i}$ (i=1, 2, ... ) based on the difference between pixel values of each pair of corresponding pixels of the images (#13).

The independent component analysis unit 22 carries out the independent component analysis for each pair of corresponding subsets $E_{1i}$ and $E_{2i}$ to calculate the separation factors $W_i$. Namely, first, "1" is set for the suffix i (#14), and the independent component analysis is carried out on inputted subsets $E_{11}$ and $E_{21}$, and separation factors $W_1$ are calculated for the subsets $E_{11}$ and $E_{21}$ (#15). Then, the suffix i is incremented by one (#16). If the suffix i has not exceeded a maximum value $I_{MAX}$, i.e., the total number of the subsets (#17: NO), separation factors $W_2$ are calculated for the next pair of subsets $E_{12}$ and $E_{21}$. Similarly, the operation to increment the suffix i (#16), and the operation to calculate the separation factors $W_i$ for inputted subsets $E_{1i}$ and $E_{2i}$ (#15) are repeated until the value of the suffix i exceeds the maximum value $I_{MAX}$.

If the value of the suffix i has exceeded the maximum value $I_{MAX}$ (#17: YES), then, the component image generating unit 23 calculates weighted sums for each corresponding pixel using the separation factors $W_i$ calculated for the pair of corresponding subsets $E_{1i}$ and $E_{2i}$. Thus, the two component images S and B representing the soft part component and the bone component are generated (#18).

The generated component images S and B are displayed on the display monitor of the image interpretation workstation 3, and are used for image interpretation by the imaging diagnostician.

As described above, in the medical information system incorporating the image component separation device according to the second embodiment of the invention, the subset classifying unit 24 classifies the pixels of the radiographic images $E_1$ and $E_2$ into the more than one subsets $E_{1i}$, $E_{2i}$ (i=1, 2, ... ) based on a difference between pixel values of each pair of corresponding pixels of the inputted two radiographic images $E_1$ and $E_2$, the independent component analysis unit 22 carries out the independent component analysis for each pair of the classified subsets $E_{1i}$ and $E_{2i}$, and the obtained separation factors $W_i$ is used by the component image generating unit 23 to calculate weighted sums of the radiographic images for each pair of the subsets $E_{1i}$ and $E_{2i}$ to generate the component images S and B representing the soft part component and the bone part component. This eliminates the influence of the beam hardening, which is inherent to radiographic images, and allows separation of the image components to be separated with higher accuracy.

It should be noted that, in this embodiment, the subset classifying unit 24 may extract only a single pair of subsets $E_{11}$ and $E_{21}$ from the images $E_1$ and $E_2$, the independent component analysis unit 22 may carry out the independent component analysis on the single pair of subsets $E_{11}$ and $E_{21}$ to calculate the separation factors $W_1$, and the separation factors $W_1$ may be applied to the entire images.

FIG. 7 is a block diagram schematically illustrating the configuration of and data flow in an image component separation device according to a third embodiment of the invention. As shown in the drawing, this device includes a nonlinear independent component analysis unit 25 and a component image generating unit 23'.

The nonlinear independent component analysis unit 25 carries out nonlinear independent component analysis using a model which represents the mixing factors (the mixing factors represent the mixing ratios of the image components of the soft parts and the bone parts in the inputted two radiographic images) as a predetermined function using, as a parameter, a difference between pixel values of each pair of corresponding pixels of the inputted two radiographic images, to calculate the separation factors.

Assuming that the inputted two images are $E_1$ and $E_2$, the image components representing the soft part component and the bone component to be separated are S and B, and the mixing factors (attenuation coefficients) for these image components are a, b, c and d, then, relationships as expressed by equations (17) and (18) below are established, as described above:

$$\begin{cases} E_1 = aS + bB \\ E_2 = cS + dB \end{cases} \quad (17), (18)$$

Transforming equations (17) and (18) to obtain the soft part image aS and the bone part image bB corresponding to the image $E_1$, equations (19) and (20) below are obtained:

$$aS = \left(E_1 - \frac{b}{d}E_2\right) \Big/ \left(1 - \frac{bc}{ad}\right) \quad (19), (20)$$

$$bB = \left(E_1 - \frac{a}{c}E_2\right) \Big/ \left(1 - \frac{ad}{bc}\right)$$

$$(= E_1 - aS).$$

It is known, as mentioned above, that the attenuation coefficient is dependent on a difference between logarithmic amounts of the inputted two radiographic images, i.e., a difference between pixel values of each pair of corresponding pixels (see U.S. Pat. No. 6,421,419). Therefore, to express the respective attenuation coefficients with using functions $f_a$, $f_b$, $f_c$ and $f_d$ of the logarithmic radiation amount difference $E_{1-2}$, equations (17) and (18) are rewritten as equations (21) and (22) below:

$$\begin{cases} E_1 = f_a(E_{1-2})S + f_b(E_{1-2})B \\ E_2 = f_c(E_{1-2})S + f_d(E_{1-2})B \end{cases} \quad (21), (22)$$

Equations (21) and (22) imply that the mixing factors in the independent component analysis are not always constant, and therefore, a linear independent component analysis algorithm such as the above-described Fast ICA cannot be applied.

Figure 8A:
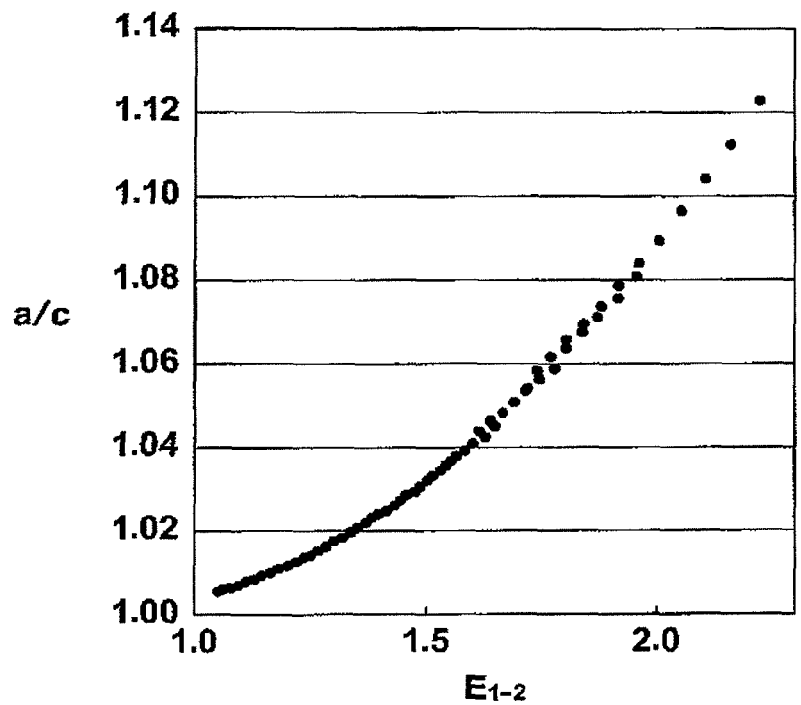
FIGS. 8A and 8B show one example of a relationship between a ratio between attenuation coefficients of each component in two radiographic images and a logarithmic radiation amount difference.
Figure 8B:
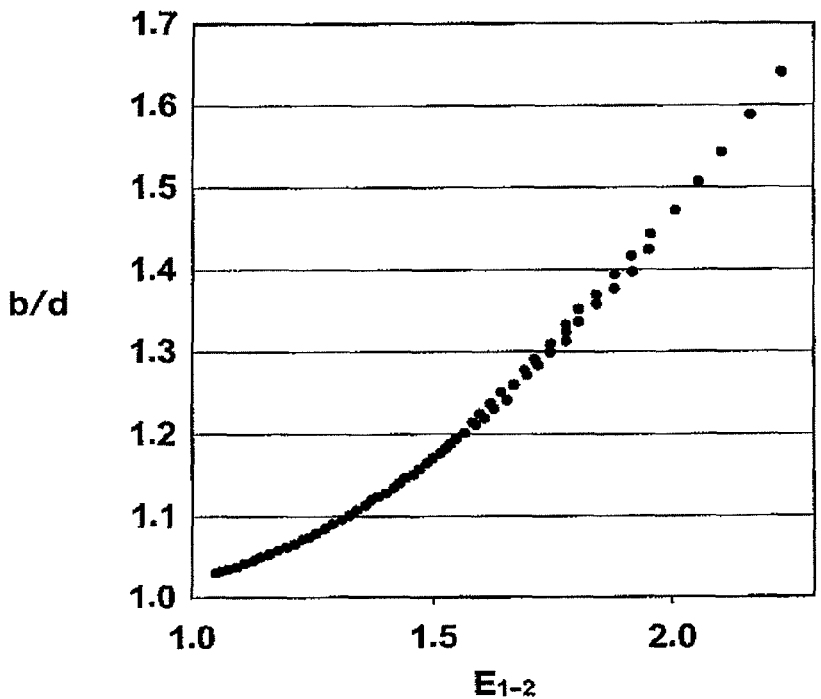

Here, focusing on the ratio a/c between the attenuation coefficients of the soft part in the two images and the ratio b/d between the attenuation coefficients of the bone part in the two images in equations (19) and (20), relationships between these ratios and the logarithmic radiation amount difference $E_{1-2}$ obtained through experiments are as shown in FIGS. 8A and 8B.

Approximating that the ratios a/c and b/d between the attenuation coefficients are linear with respect to the logarithmic radiation amount difference $E_{1-2}$, for the sake of simplicity, $a/c = e + fE_{1-2}$ and $b/d = g + hE_{1-2}$. Then, equations (19) and (20) are rewritten as equations (23) and (24) below:

$$\begin{cases} aS = \dfrac{E_1 - (g + hE_{1-2})E_2}{1 - (g + hE_{1-2})/(e + fE_{1-2})} \\ bB = \dfrac{E_1 - (e + fE_{1-2})E_2}{1 - (e + fE_{1-2})/(g + hE_{1-2})} \end{cases} \quad (23), (24)$$

Thus, the independent components aS and bB can be estimated from the two images $E_1$ and $E_2$ by optimizing the parameters e, f, g and h such that mutual information between aS and bB is minimized.

Assuming that aS=S' and bB=B', then the mutual information I (S',B') between S' and B' can be obtained according to equation (25) below:

$$I(S', B') = \\ H(S') + H(B') - H(S', B') = \sum_{i,j} P_{S'B'}(i,j) \times \log \dfrac{P_{S'B'}(i,j)}{P_{S'}(i)P_{B'}(j)} \quad (25)$$

where H represents entropy, $P_{S'}$, and $P_{S'}$ respectively represent marginal probability distributions of S' and B', and $P_{S'B'}$ represents a joint probability distribution of S' and B'. That is, $P_{S'}(i)$ represents a probability of S' taking a pixel value of "i", which is obtained by "a number of pixels that take a pixel value of "i"/ a total number of pixels of the image data (S')" from a histogram of the image data (S'). $P_{B'}(j)$ represents a probability of B' taking a pixel value of "j", and $P_{S'B'}(i,j)$ represents a probability of S' taking a pixel value of "i" and B' taking a pixel value of "j", which are obtained in the similar manner to that for obtaining $P_{S'}(i)$. It should be noted that, since $P_{S'B'}(i,j)$ contains the two probability variables "i" and "j", a two-dimensional histogram is used.

The values of the parameters e, f, g and h for minimizing the mutual information I (S',B') can be determined by using, for example, simplex procedure.

Figure 9A:
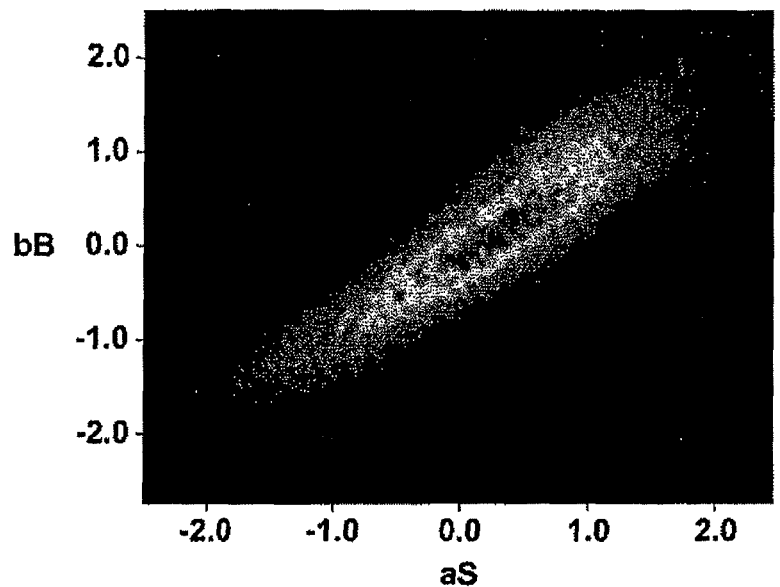
FIGS. 9A and 9B show one example of frequency distributions of components to be separated for calculating mutual information.
Figure 9B:
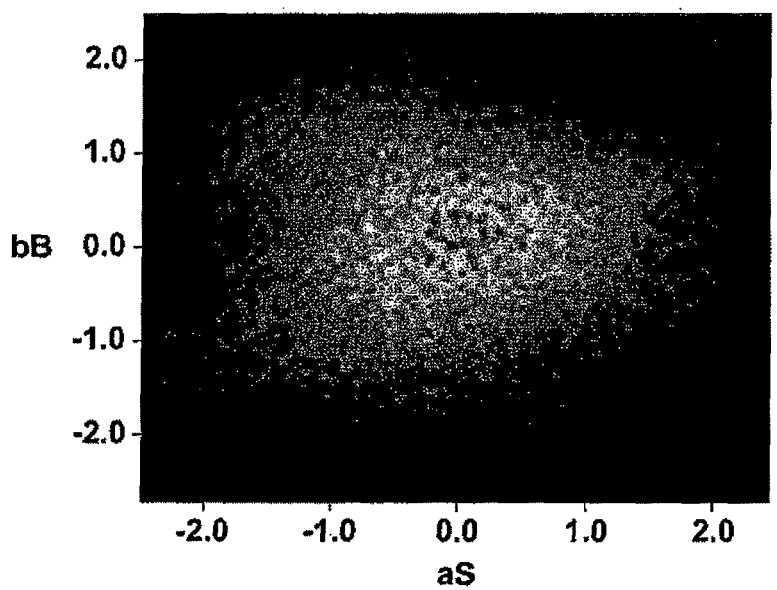
Figure 10A:
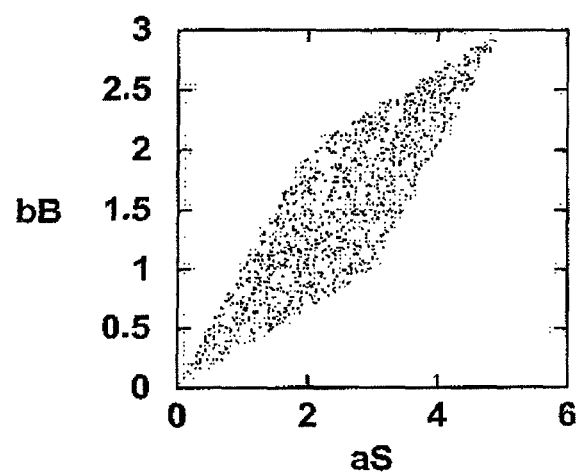
FIGS. 10A and 10B show one example of different distributions of two variables for different amounts of mutual information between these variables (10A shows a case where the mutual information=0.8 and 10B shows a case where the mutual information=0)
Figure 10B:
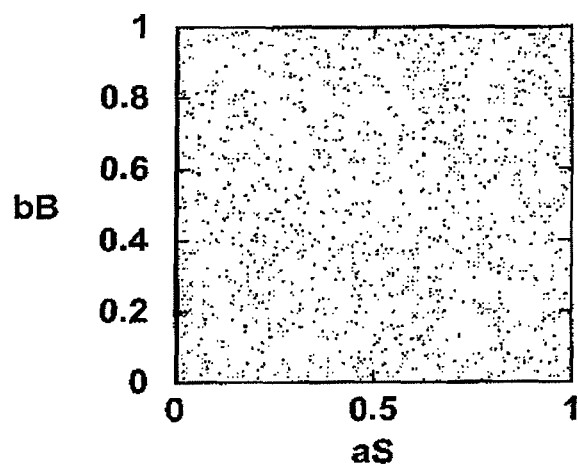

FIGS. 9A and 9B show one example of frequency distributions of S' and B' for calculating the mutual information. FIG. 9A shows a frequency distribution when the initial values are set for the parameters e, f, g and h, and FIG. 9B shows a frequency distribution after the parameters e, f, g and h are optimized. FIG. 10A shows a distribution of the two variables in a case where the value of the mutual information between the variables is about 0.8, and FIG. 10B shows a distribution of the two variables in a case where the value of the mutual information between the variables is 0. By minimizing the mutual information in this manner, correlation between the two variable S' and B' is lowered and thus these variables become components with higher independence.

It should be noted that the relationship between the logarithmic radiation amount difference $E_{1-2}$ and each of the ratios a/c and b/d of the attenuation coefficients may not be approximated as being linear, and may be approximated with a quadratic function, for example.

The component image generating unit 23' assigns the values of the parameters e, f, g and h obtained by the nonlinear independent component analysis unit 25 and the difference $E_{1-2}$ between pixel values of each pair of corresponding pixels of the inputted images $E_1$ and $E_2$ to equations (23) and (24) to calculate a pixel value of each pixel of the soft part image S and the bone part image B.

Now, workflow and data flow of the image interpretation using an image component separation process according to the third embodiment of the invention are described with reference to the flow chart shown in FIG. 11 and the block diagram shown in FIG. 7.

First, similarly to the first embodiment, user authentication of the imaging diagnostician is carried out (#21), and the imaging diagnostician selects and obtains the images $E_1$ and $E_2$ to be interpreted (#22). Then, the image interpretation workstation 3 starts a program of the image component separation device according to the third embodiment of the invention based on contents of an image diagnosis order.

According to the started program, the nonlinear independent component analysis unit 25 applies the above-described nonlinear independent component analysis to the inputted images $E_1$ and $E_2$ and calculates the separation factors W (the parameters e, f, g and h) (#23), and the component image generating unit 23' generates the two component images S and B representing the soft part component and the bone component by calculating a pixel value of each pixel of the soft part image S and the bone part image B based on the separation factors W and the difference $E_{1-2}$ between pixel values of each pair of corresponding pixels of the images $E_1$ and $E_2$ (#24).

The generated component images S and B are displayed on the display monitor of the image interpretation workstation 3, and are used for image interpretation by the imaging diagnostician.

As described above, in the medical information system incorporating the image component separation device according to the third embodiment of the invention, the nonlinear independent component analysis unit 25 carries out the nonlinear independent component analysis using the model which represents the mixing factors representing the mixing ratios of the image components of the soft parts and the bone parts in the inputted two radiographic images $E_1$ and $E_2$ as a predetermined function using, as a parameter, the difference $E_{1-2}$ between pixel values of each pair of corresponding pixels of the inputted two radiographic images $E_1$ and $E_2$, to calculate the separation factors W with taking the influence of the beam hardening inherent to the radiographic images into account. Using the thus obtained separation factors W, separation of the image components to be separated can be achieved with higher accuracy.

Figure 14:
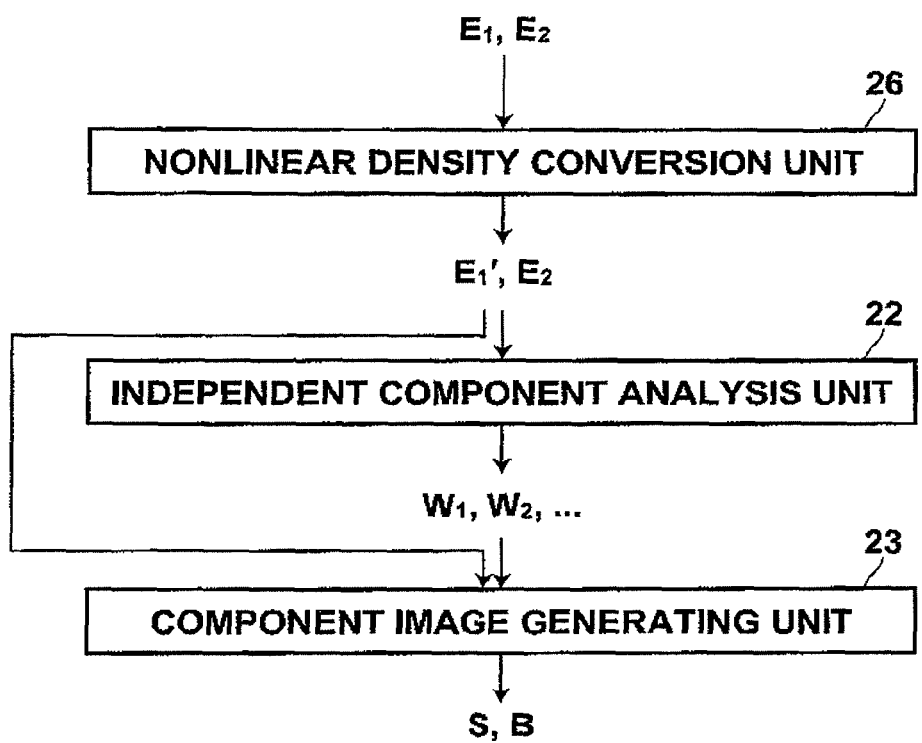
FIG. 14 is a block diagram schematically illustrating the configuration of an image component separating device and peripheral elements according to a fourth embodiment of the invention.

FIG. 14 is a block diagram schematically illustrating the configuration of and data flow in an image component separation device according to a fourth embodiment of the invention. As shown in the drawing, this device includes a nonlinear density conversion unit 26, the independent component analysis unit 22 and the component image generating unit 23.

In this embodiment, it is assumed that the radiographic images $E_1$ and $E_2$ are obtained by a two-shot method, i.e., obtained through two exposures to radiations having different energy distributions, and the image $E_1$ is formed with the radiation having the higher energy distribution than that used for forming the image $E_2$. Hereinafter, the image $E_1$ is referred to as the higher energy image $E_1$ and the image $E_2$ is referred to as the lower energy image $E_2$.

Figure 15:
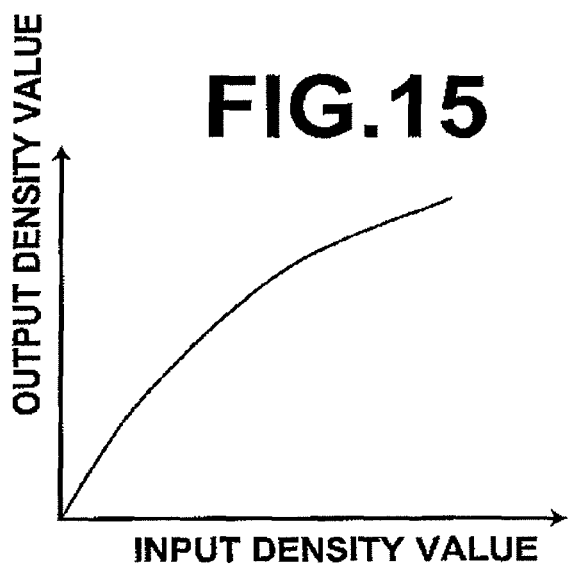
FIG. 15 shows one example of a look-up table for carrying out nonlinear density conversion.

The nonlinear density conversion unit 26 carries out nonlinear density conversion on the higher energy image $E_1$ to relatively increase the gain in a region having larger radiation attenuation, i.e., a region where the density value of the image is smaller (whiter), so that the gain in the region in the higher energy image $E_1$ becomes larger than the gain in the lower energy image $E_2$, and outputs a higher energy image $E_1'$ subjected to the density conversion. FIG. 15 schematically illustrates a look-up table (LUT) used for carrying out the density conversion. As can be seen, the conversion is carried to provide a "steeper" gradation at the lower density side. In this embodiment, it is assumed that the density conversion is not carried out on the lower energy image $E_2$, or a linear density conversion is carried out on the lower energy image $E_2$. The higher energy image of the radiographic images $E_1$ and $E_2$ may be determined by referencing information, such as a tube voltage, contained in the accompanying information of each image, or may be specified by the user in advance.

As mentioned previously, the two radiographic images obtained by the two-shot method do not have a relationship where a ratio between the radiation attenuations in the two radiographic images is constant regardless of the thickness of the components and the thickness of the subject, since the higher energy image $E_1$ has lower linearity between the X-ray exposure amount (log) and the thickness of the subject or the components of the subject than the linearity in the lower energy image $E_2$ due to influences of the beam hardening and the Compton scattering. This acts as noise in the following estimation of the independent components in the independent component analysis.

The nonlinear density conversion is carried out to reduce influence of this effect acting as noise. By carrying out the above-described density conversion on the higher energy image $E_1$ with focusing on a relationship that the smaller the pixel value (density value) of a region in the radiographic image (the higher energy image $E_1$ is used in this embodiment), the greater the thickness of the subject in that region, correction to bring the images closer to achieving the relationship where the ratio between the radiation attenuations in the two radiographic images is constant regardless of the thickness of the components and the thickness of the subject is achieved.

Operations carried out by the independent component analysis unit 22 and the component image generating unit 23 are the same as those described in the first embodiment.

Now, workflow and data flow of the image interpretation using an image component separation process according to the fourth embodiment of the invention are described with reference to the flow chart shown in FIG. 16 and the block diagram shown in FIG. 14.

First, similarly to the first embodiment, user authentication of the imaging diagnostician is carried out (#31), and the imaging diagnostician selects and obtains images $E_1$ and $E_2$ to be interpreted (#32). Then, the image interpretation workstation 3 starts a program of the image component separation device according to the fourth embodiment of the invention based on contents of an image diagnosis order.

According to the started program, the nonlinear density conversion unit 26 applies the nonlinear density conversion to the higher energy image $E_1$ of the inputted radiographic images $E_1$ and $E_2$, and outputs the converted higher energy image $E_1'$ (#33).

The independent component analysis unit 22 carries out the independent component analysis on the converted higher energy image $E_1'$ and the lower energy image $E_2$ inputted thereto, which correspond to the observation signals, and calculates the separation factors W for separating the soft part component and the bone component, which correspond to the independent components, from the images (#34). The component image generating unit 23 uses the separation factors W as the weighting factors to calculate weighted sums of each corresponding pixel between the converted higher energy image $E_1'$ and the lower energy image $E_2$, to generate the two component images S and B representing the soft part component and the bone component (#35).

The generated component images S and B are displayed on the display monitor of the image interpretation workstation 3, and are used for image interpretation by the imaging diagnostician.

As described above, in the medical information system incorporating the image component separation device according to the fourth embodiment of the invention, the nonlinear density conversion unit 26 applies the nonlinear density conversion to the higher energy image $E_1$ to relatively increase the gain in a region having larger radiation attenuation, i.e., a region where the density value of the image is smaller (whiter), so that the gain in the region in the higher energy image $E_1$ becomes larger than the gain in the lower energy image $E_2$, the independent component analysis unit 22 carries out the independent component analysis on the converted higher energy image $E_1'$ and the lower energy image $E_2$, which correspond to the observation signals, to calculate the separation factors W, and the component image generating unit 23 uses the separation factors W as the weighting factors to generate the component images S and B representing the soft part component and the bone part component. This eliminates the influence of the beam hardening inherent to radiographic images, thereby allowing separation of the image components to be separated with higher accuracy.

FIG. 17 schematically shows a change in the relationship between the logarithmic X-ray exposure amount (density of each radiographic image) and the thickness of the subject achieved by the above-described nonlinear density conversion. As can be seen, before the correction by the nonlinear density conversion unit 26 (indicated by the short dashed line), a ratio between an X-ray attenuation $E_H$ in the higher energy image $E_1$ and an X-ray attenuation $E_L$ in the lower energy image $E_2$ varies depending on the thickness of the subject. In contrast, after the correction by the nonlinear density conversion unit 26 (indicated by the alternate long and short dash line), the ratio between the X-ray attenuation $E_H$ in the higher energy image $E_1$ and the X-ray attenuation $E_L$ in the lower energy image $E_2$ is nearly constant.

Figure 18:
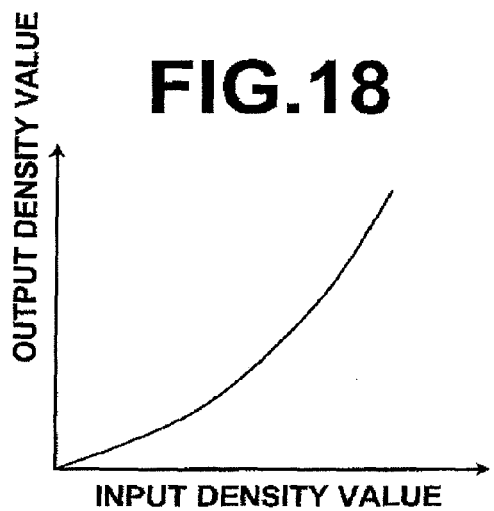
FIG. 18 shows another example of the look-up table for carrying out nonlinear density conversion.

It should be noted that, the nonlinear density conversion unit 26 in this embodiment may use a look-up table schematically shown in FIG. 18 to apply nonlinear density conversion to the lower energy image $E_2$ to relatively decrease the gain in a region having larger radiation attenuation (a region where the density values of the image is smaller (whiter)) so that the gain in the region in the lower energy image $E_2$ becomes smaller than the gain in the higher energy image $E_1$ (i.e., to provide a "gentler" gradation). In this case, the higher energy image $E_1$ may not be subjected to density conversion, may be subjected to linear density conversion, or may be subjected to the nonlinear density conversion shown in FIG. 15.

Figure 19:
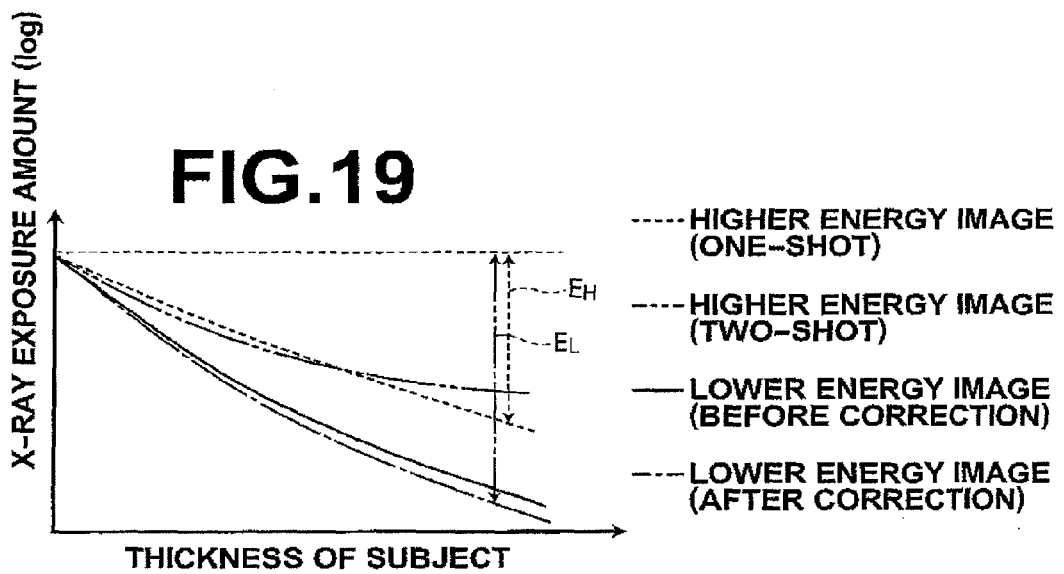
FIG. 19 shows a relationship between the thickness of the subject and the X-ray exposure amount (log) with respect to radiographic images obtained through a one-shot method.

Further, in this embodiment, the two radiographic images to be inputted are obtained through the two-shot method. In a case of radiographic images obtained through a one-shot method, direction of the nonlinear density conversion is different. For example, when images are formed on two IPs with a copper plate disposed therebetween by being exposed to radiation once, as an example of the one-shot method using a CR apparatus, a higher energy image (which was placed behind the copper plate) has higher linearity than a lower energy image (which was placed before the copper plate), as can be seen from a relationship between the logarithmic X-ray exposure amount and the thickness of the subject schematically shown in FIG. 19 (the short dashed line indicates the higher energy image and the solid line indicates the lower energy image obtained in the one-shot method). This is because that, in the one-shot method, nearly the same level of influence is exerted by scattered radiation both to the higher and lower energy images, and the higher energy image has higher monochromaticity due to the fact that the radiation has transmitted through the copper plate, and therefore the influence of beam hardening is greater in the lower energy image than in the higher energy image.

Therefore, in the case of the radiographic images obtained by the one-shot method, it is necessary to carry out density conversion which is inverse to that carried out on the images obtained by the two-shot method. Namely, in this case, the nonlinear density conversion unit 26 uses the look-up table schematically shown in FIG. 15 to apply the nonlinear density conversion to the lower energy image $E_2$ to relatively increase the gain in the region having larger radiation attenuation, i.e., the region where the density value of the image is smaller (whiter), so that the gain in the region in the lower energy image $E_2$ becomes larger than the gain in the higher energy image $E_1$ (i.e., to provide a "steeper" gradation). Thus, the logarithmic X-ray exposure amount in the lower energy image $E_2$ is changed as indicated by the alternate long and short dash line in FIG. 19. After the conversion, the ratio between the X-ray attenuation $E_H$ in the higher energy image $E_1$ and the X-ray attenuation $E_L$ in the lower energy image $E_2$ is nearly constant regardless of the thickness of the subject. Therefore, similarly to the case of the radiographic images obtained by the two-shot method, the influence of the beam hardening inherent to radiographic images can be eliminated and separation of the image components to be separated with higher accuracy can be achieved.

Alternatively, the nonlinear density conversion unit 26 may use the look-up table schematically shown in FIG. 18 to apply the nonlinear density conversion to the higher energy image $E_1$ to relatively decrease the gain in the region having larger radiation attenuation, i.e., a region where the density value of the image is smaller (whiter), so that the gain in the region in the higher energy image $E_1$ becomes smaller than the gain in the lower energy image $E_2$ (i.e., to provide a "gentler" gradation).

Furthermore, in this embodiment, although the component image generating unit 23 generates the two component images S and B representing the soft part component and the bone component from the density-converted higher energy image $E_1'$ and the lower energy image $E_2$, the component image generating unit 23 may generate the component images S and B from the radiographic image $E_1$ before the density conversion and the radiographic image $E_2$.

In the above-described embodiments, although the process to separate the two image components representing the two components including the soft parts and the bones is carried out on the inputted two radiographic images, the above-described embodiments may be applied to a process for separating three or more image components representing three or more components from three or more inputted radiographic images. In this case, the number of components to be separated has to be not more than the total number of radiographic images to be inputted.

It may also be considered that, in the above-described embodiments, a region containing the bones may be detected using a known image recognition process, and images of the region containing the bones together with the soft parts may be used as the input for the independent component analysis. By inputting the images containing both the independent components to be separated (soft parts and bones) in this manner, the precondition on the observation signals in the independent component analysis that the observation signals have to contain all the component signals to be separated can more appropriately be satisfied, and therefore separation of the image components to be separated with higher accuracy can be achieved.

Alternatively, the user may specify the region on which he or she wants to carry out the separation, and the specified region may be used as the input to carry out the independent component analysis.

Further, regions in the radiographic images to be inputted where the radiation has scarcely attenuated and regions where most of the radiation has attenuated may be excluded. This removes regions which act as noise to the independent components, such as soft parts and bones, to be separated during the independent component analysis, thereby improving accuracy of the separation.

It should be noted that, besides the description given above, various modifications made on the system configurations, the process flows, the table structures, the user interfaces, or the like, of the embodiments without departing from the spirit and scope of the invention are intended to be encompassed within the technical scope of the invention. Further, the above-described embodiments are provided only by way of examples, and should not be construed as limiting the technical scope of the invention.

Figure 20:
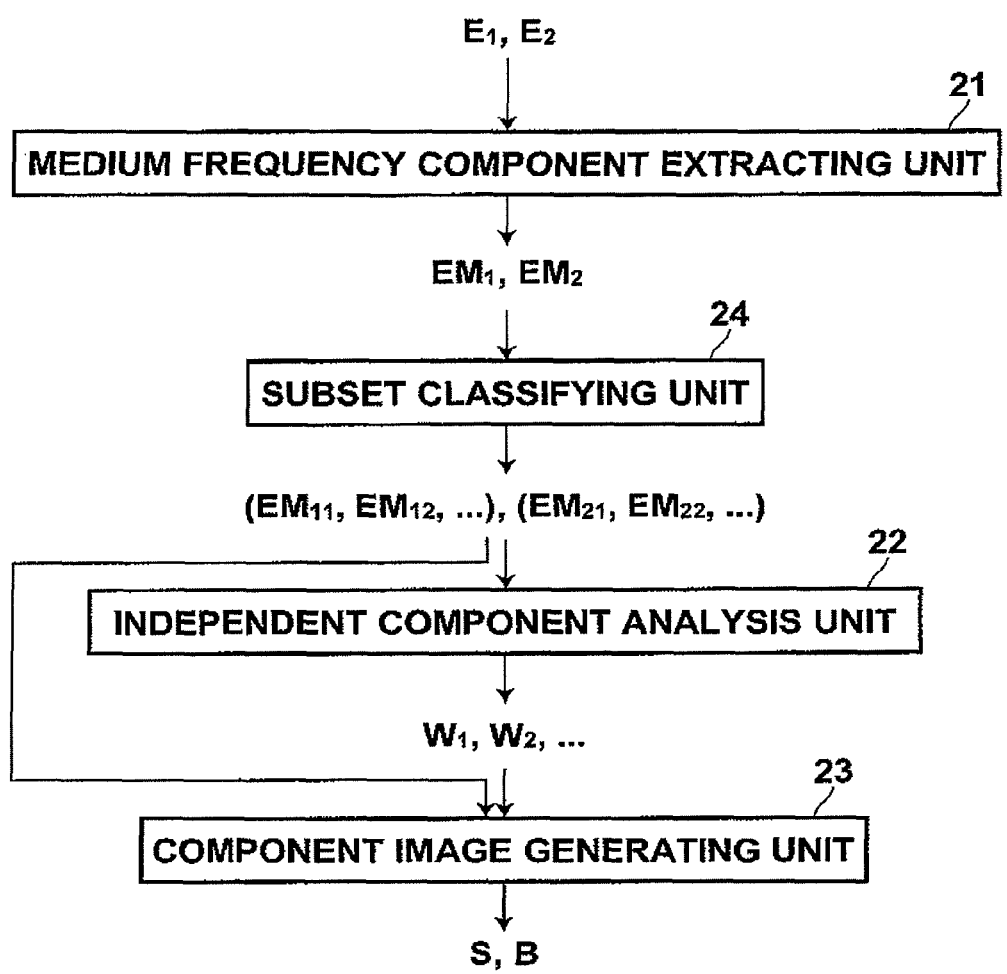
FIG. 20 is a block diagram schematically illustrating the configuration of an image component separating device and peripheral elements according to a modification made on the embodiments of the invention.

For example, as shown in the block diagram of FIG. 20, the first embodiment and the second embodiment may be combined so that the medium frequency component extracting unit 21 extracts the image components $EM_1$ and $EM_2$ of the medium frequency band from the inputted radiographic images $E_1$ and $E_2$, the subset classifying unit 24 classifies the pixels of the image components $EM_1$ and $EM_2$ into more than one subsets $EM_{1i}$, $EM_{2i}$ (i=1, 2, . . . ) based on a difference between pixel values of each pair of corresponding pixels of the extract image components $EM_1$ and $EM_2$ of the medium frequency band, the independent component analysis unit 22 carries out the independent component analysis for each of the classified subsets $EM_{1i}$, $EM_{2i}$, and the component image generating unit 23 uses the obtained separation factors $W_i$ to calculate weighted sums of the radiographic images for each of the subsets $E_{1i}$ and $E_{2i}$ of the inputted images $E_1$ and $E_2$, which correspond to the subsets $EM_{1i}$ and $EM_{2i}$ of the medium frequency band, to generate the component images S and B representing the soft part component and the bone part component.

Figure 21:
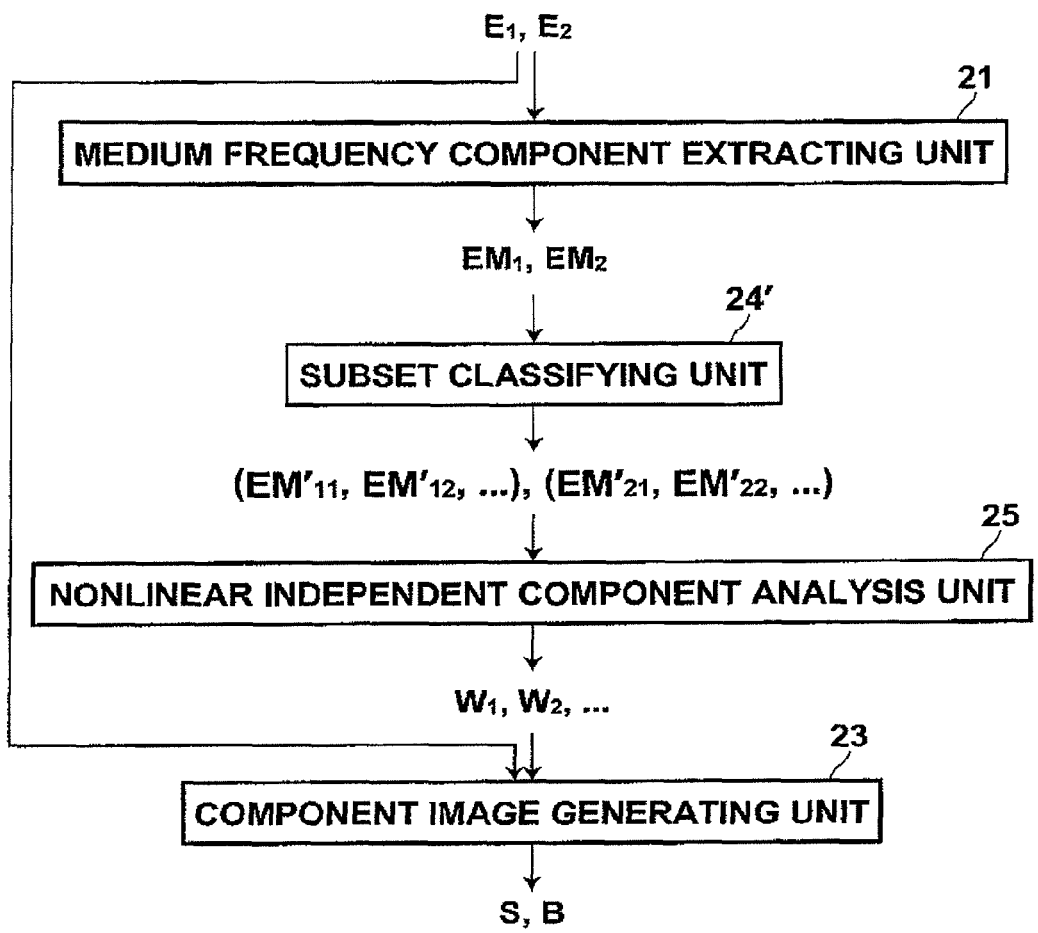
FIG. 21 is a block diagram schematically illustrating the configuration of an image component separating device and peripheral elements according to another modification made on the embodiments of the invention.

Moreover, as shown in the block diagram of FIG. 21, the third embodiment may further be combined to the above combination of the first and second embodiments so as to carry out the nonlinear independent component analysis for each subset of the medium frequency band. In this case, the subset classifying unit 24' may reference, for example, the table shown in FIG. 8 representing the relationship between the logarithmic radiation amount difference $E_{1-2}$ and each of the ratio a/c of the attenuation coefficients of the soft parts and the ratio b/d of the attenuation coefficients of the bone parts, and may classify the image components $EM_1$, $EM_2$ of the medium frequency band into a subset of regions which have a closer-to-linear relationship between the attenuation coefficients and the logarithmic radiation amount difference $E_{1-2}$ and a subset of regions other than the above regions.

Furthermore, as shown in the block diagram of FIG. 22, the first, second and fourth embodiments may be combined so that the nonlinear density conversion unit 26 applies the nonlinear density conversion to the higher energy image $E_1$ to relatively increase the gain in the region having larger radiation attenuation, i.e., the region where the density values of the image are smaller (whiter), so that the gain in the region in the higher energy image $E_1$ becomes larger than the gain in the lower energy image $E_2$, the medium frequency component extracting unit 21 extracts the image components $EM_1'$ and $EM_2$ of the medium frequency band from the density-converted radiographic image $E_1'$ and the lower energy image $E_2$, the subset classifying unit 24 classifies the pixels of the extracted image components $EM_1'$ and $EM_2$ into more than one subsets $EM_{1i}'$, $EM_{2i}$ (i=1, 2, ... ) based on a difference between pixel values of each pair of corresponding pixels of the image components $EM_1'$ and $EM_2$ of the medium frequency band, the independent component analysis unit 22 carries out the independent component analysis for each of the classified subsets $EM_{1i}'$, $EM_{2i}$, and the component image generating unit 23 uses the obtained separation factors $W_i$ to calculate weighted sums of the radiographic images for each of the subsets $E_{1i}'$ and $E_{2i}$ of the images $E_1'$ and $E_2$ corresponding to the subsets $EM_{1i}'$ and $EM_{2i}$ of the medium frequency band to generate the component images S and B representing the soft part component and the bone part component.

It should be noted that, in the above description, it is assumed that logarithmic conversion is applied to the obtained images before the operations by the units 21-26 are carried out, and therefore, the process for separating the component images carried out by the component image generating unit 23 is expressed as the "weighted sum". However, if the component images are separated from images which have not been subjected to the logarithmic conversion, it is apparent that the same results as in the above description can be obtained by reading the "sum" in the above description as "product", and the "difference" as "quotient".

In the first aspect of the invention, before obtaining the separation factors for separating the more than one image components from the more than one radiographic images using the independent component analysis, an image component of a spatial frequency band containing each of the more than one components is extracted from each of the radiographic images, the independent component analysis is carried out on the extracted image component, and the obtained separation factors are used to calculate a weighted sum of the radiographic images to separate each of the more than one image components respectively representing more than one predetermined components in the subject. The extracted image components of the spatial frequency bands more appropriately satisfy the precondition on the observation signals in the independent component analysis that the observation signals have to contain all the component signals to be separated, and thus separation of the image components to be separated with higher accuracy can be achieved.

For example, in a case where image components representing the bone component and the soft part component are separated from the radiographic images of a human body, image component of the medium frequency band including the spatial frequency band corresponding to the thickness of the bone of the human body can be extracted so that the low frequency band where the bone part component is scarcely present (a spatial frequency band corresponding to structures which are thicker than the thickness of the bone of the human body) and the high frequency band where noise is dominant are excluded from the data inputted for the independent component analysis, and only the image component of the medium frequency band where much of the bone component and the soft part component are present is inputted. This minimizes influence of noise in the independent component analysis, and increases robustness of the operation to obtain the separation factors. Explaining from a different point of view, in the human body, the bones are usually not present where no soft tissue is present, and the bones are likely to be present where the soft tissues are relatively thick. That is, these two tissues have a strong correlation in the low frequency band, and this lowers the independence between these tissues. Therefore, by removing the frequency band which is lower than the frequency band corresponding to the thickness of the bone, the independence between these two tissues can be increased, thereby facilitating the separation.

In radiographic images obtained by actual imaging, if the radiation applied to the subject is not monochromatic and is distributed over a certain energy range, a phenomenon called beam hardening occurs, in which the energy distribution of the applied radiation varies depending on the thickness of each component in the subject, and therefore, the attenuation coefficient in each component differs from pixel to pixel. Explaining in more detail, the attenuation coefficient in an X-ray energy range in which the Compton effect is dominant (an X-ray energy range in typical imaging of around 40-150 kVp) monotonically decreases as the thickness of other components increases. For example, in a case of the chest of the human body, the attenuation coefficient within the lung field differs from that in the mediastinum. In the (linear) independent component analysis, if the component signals are mixed with different mixing factors in a single observation signal, subsets of the component signals mixed with the different mixing factors act as noise to each other during estimation of the independent components.

Therefore, according to the second aspect of the invention, before the independent component analysis is applied to obtain the separation factors for separating the more than one image components from the radiographic images, pixels of the radiographic images are classified into one or more subsets for each of the radiographic images based on a value of a parameter, which is obtained from at least one of the radiographic images, having a predetermined relationship with the thickness of each of the more than one predetermined components or the thickness of the subject at each pixel of each of the radiographic images. Then, the independent component analysis is carried out on at least one pair of the classified subsets of the radiographic images. The obtained separation factors are used to calculate weighted sums of the radiographic images or each pair of the subsets to separate the more than one image components respectively representing the more than one predetermined components in the subject. This prevents the component signals mixed with different mixing factors due to the influence of the beam hardening, which is inherent to the radiographic images, from acting as noise, and allows separation of the image components to be separated with higher accuracy.

According to the third aspect of the invention, when the separation factors for separating the more than one image components from the radiographic images are obtained using the independent component analysis, the model representing the mixing factors, which represents the mixing ratios between the more than one image components in the radiographic images, as a predetermined function using a parameter, which is obtained from at least one of the radiographic images and has a predetermined relationship with the thickness of each of the more than one predetermined components or the thickness of the subject at each pixel of the radiographic images, is used. Therefore, the nonlinear independent component analysis is carried out with taking the influence of the beam hardening inherent to radiographic images into account, thereby allowing separation of the image components to be separated with higher accuracy.

In a case of radiographic images formed by the multi-shot method, the decrease rate of the X-ray exposure amount decreases as the thickness of the subject increases due to the influence of beam hardening, as can be seen from the relationship between the thickness of the subject and the X-ray exposure amount schematically shown in FIG. 13. Therefore, the relationship between the X-ray exposure amount (log) and the thickness of the subject or each component of the subject is not linear both in the image formed with higher energy X-ray and the image formed with lower energy X-ray. Further, since the X-ray at the higher energy side at which the Compton effect is more dominant generates more scattered radiation, the scattered radiation increases as the thickness of the subject increases, and the decrease rate of the X-ray exposure amount becomes further smaller than the X-ray at the lower energy side. The alternate long and short dash line in FIG. 13 represents a case where the scattered radiation of the X-ray at the higher energy side is about the same as that of the lower energy side, and the short dashed line in FIG. 15 represents a case of the X-ray at the higher energy side containing actual scattered radiation.

On the other hand, as described above, it is assumed in the (linear) independent component analysis that the component signals contained in a single observation signal are mixed with the same mixing factor, and component signals mixed with different mixing factors in a single observation signal act as noise to each other during estimation of the independent components.

Therefore, the fourth aspect of the invention focuses on the fact that, when the image components in the radiographic images are separated, even if the component signals in a single observation signal are not mixed with the same mixing factor, it suffices if a condition that the ratio between radiation attenuations in the radiographic images is constant regardless of the thickness of each component or the thickness of the subject is satisfied. In the fourth aspect of the invention, a pixel value of each pixel of at least one of the radiographic images is nonlinearly converted based on a value of a parameter having a predetermined relationship with the thickness of each of the more than one predetermined components or the thickness of the subject at each pixel of the radiographic images so that the images are brought closer to achieving the above-described condition. This prevents the component signals mixed with different mixing factors from acting as noise, and allows separation of the image components to be separated with higher accuracy.

As described above, according to the invention, the problem inherent to radiographic images, which may occur when the independent component analysis technique is applied to energy subtraction carried out on radiographic images, is solved, and separation of the image components to be separated with higher accuracy can be achieved.

What is claimed is:

1. An image component separation device, comprising:
component separating means for separating bone and soft tissues as predetermined components from more than one radiographic images inputted thereto, the image components respectively representing more than one predetermined components in a site to be examined of a human body, each radiographic image being formed by radiation transmitted through the site to be examined of a human body, each radiographic image representing degrees of transmission and attenuation through the site to be examined of a human body of each of different patterns of radiation having different energy distributions, the component separating means separating the image components by calculating weighted sums using predetermined weighting factors for each corresponding pixel among the radiographic images, wherein the component separating means carries out independent component analysis on the radiographic images to obtain separation factors for separating the bone and soft tissues as predetermined components from the radiographic images and uses the separation factors as the predetermined weighting factors, and the independent component analysis is carried out with using a model representing, as a predetermined function, mixing factors representing mixing ratios of the bone and soft tissues as predetermined components in each of the radiographic images using a parameter obtained from at least one of the radiographic images, the parameter having a predetermined relationship with a thickness of each of the more than one predetermined components or a thickness of the site to be examined of a human body at each pixel of the ratio graphic images.

2. The image component separation device according to claim 1,
wherein the parameter is any one of a radiation amount at each pixel of one of the radiographic images, a logarithmic value of the radiation amount, a difference between logarithmic values of radiation amounts at each pair of corresponding pixels between two of the radiographic images, and a logarithmic value of a ratio between radiation amounts at each pair of the corresponding pixels.

3. An image component separation method comprising:
a component separating step to separate bone and soft tissues as predetermined components from more than one radiographic images inputted thereto, the image components respectively representing more than one predetermined components in a site to be examined of a human body, each radiographic image being formed by radiation transmitted through the site to be examined of a human body, each radiographic image representing degrees of transmission and attenuation through the site to be examined of a human body of each of different patterns of radiation having different energy distributions, the component separating step including separating the image components by calculating weighted sums using predetermined weighting factors for each corresponding pixel among the radiographic images, wherein the component separating step includes carrying out independent component analysis on the radiographic images to obtain separation factors for separating the bone and soft tissues as predetermined components from the radiographic images and using the separation factors as the predetermined weighing factors, and the independent component analysis is carried out with using a model representing, as a predetermined function, mixing factors representing mixing ratios of the bone and soft tissues as predetermined components in each of the radiographic images using a parameter obtained from at least one of the radiographic images, the parameter having a predetermined relationship with a thickness of each of the more than one predetermined components or a thickness of the site to be examined of a human body at each pixel of the radiographic images.

4. A non-transitory computer-readable recording medium containing an image component separation program for causing a computer to carry out a component separation method, said method comprising:

a component separating step to separate bone and soft tissues as predetermined components from more than one radiographic images inputted thereto, the image components respectively representing more than one predetermined components in a site to be examined of a human body, each radiographic image being formed by radiation transmitted through the site to be examined of a human body, each radiographic image representing degrees of transmission and attenuation through the site to be examined of a human body of each of different patterns of radiation having different energy distributions, the component separating step including separating the image components by calculating weighted sums using predetermined weighting factors for each corresponding pixel among the radiographic images, wherein the component separating step includes carrying out independent component analysis on the radiographic images to obtain separation factors for separating the bone and soft tissues as predetermined components from the radiographic images and using the separation factors as the predetermined weighing factors, and the independent component analysis is carried out with using a model representing, as a predetermined function, mixing factors representing mixing ratios of the bone and soft tissues as predetermined components in each of the radiographic images using a parameter obtained from at least one of the radiographic images, the parameter having a predetermined relationship with a thickness of each of the more than one predetermined components or a thickness of the site to be examined of a human body at each pixel of the radiographic images.

* * * * *